(12) United States Patent
Liu et al.

(10) Patent No.: US 8,481,327 B2
(45) Date of Patent: Jul. 9, 2013

(54) METHODS FOR USING CONGENERIC, CHLORINATED, BROMINATED AND/OR IODISED, FLUORINATED AROMATIC STANDARD COMPOUNDS HAVING TWO BENZOL RINGS

(75) Inventors: Huiling Liu, Trondheim (NO); Gregor Luthe, Gronau (DE); Jon Eigill Johansen, Trondheim (NO)

(73) Assignee: Chiron AS, Trondheim (NO)

( * ) Notice: Subject to any disclaimer, the term of this patent is extended or adjusted under 35 U.S.C. 154(b) by 0 days.

(21) Appl. No.: 13/149,616

(22) Filed: May 31, 2011

(65) Prior Publication Data

US 2011/0229973 A1    Sep. 22, 2011

Related U.S. Application Data

(62) Division of application No. 10/589,897, filed as application No. PCT/EP2005/050779 on Feb. 16, 2005, now abandoned.

(30) Foreign Application Priority Data

Feb. 16, 2004   (DE) .......................... 10 2004 007 358

(51) Int. Cl.
*G01N 33/00* (2006.01)
*G01N 30/72* (2006.01)

(52) U.S. Cl.
USPC ........... 436/124; 436/125; 436/126; 436/161; 436/173

(58) Field of Classification Search
USPC ................. 436/124–126, 161, 173; 568/639
See application file for complete search history.

(56) References Cited

U.S. PATENT DOCUMENTS

| | | | | |
|---|---|---|---|---|
| 3,959,387 A * | 5/1976 | Brackenridge | ............... | 568/639 |
| 4,020,112 A * | 4/1977 | Boswell et al. | ............... | 568/639 |
| 4,194,054 A * | 3/1980 | Forster et al. | ............... | 562/493 |
| 5,037,553 A * | 8/1991 | Del Mar et al. | ............... | 210/635 |
| 5,110,473 A * | 5/1992 | Hassett | ........................ | 210/634 |
| 6,469,187 B1 * | 10/2002 | Craven et al. | ................ | 554/195 |
| 7,989,194 B2 * | 8/2011 | Seeger Pfeiffer et al. | . | 435/252.3 |
| 7,996,156 B2 * | 8/2011 | Beger et al. | ...................... | 702/19 |
| 2003/0229456 A1 * | 12/2003 | Beger et al. | ...................... | 702/27 |
| 2004/0047834 A1 * | 3/2004 | Suzuki et al. | ................ | 424/78.1 |

OTHER PUBLICATIONS

Kende, A. S. et al, Journal of Organic Chemistry 1974, 39, 931-937.*
Barnhart, E. R. et al, Analytical Chemistry 1987, 59, 2248-2252.*
Waddell, D. et al, Chemosphere, 1990, 20, 1299-1306.*
Weber, R. et al, Chemosphere, 1997, 34, 13-28.*

* cited by examiner

*Primary Examiner* — Arlen Soderquist
(74) *Attorney, Agent, or Firm* — Lucas & Mercanti, LLP; Klaus P. Stoffel

(57) ABSTRACT

Congeneric, halogenated, fluorinated aromatic compounds

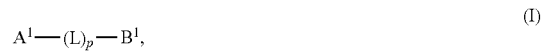

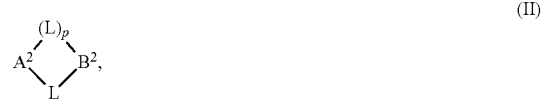

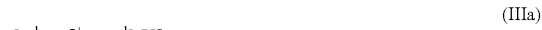

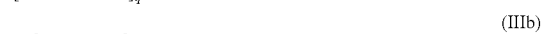

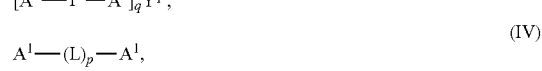

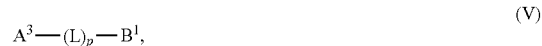

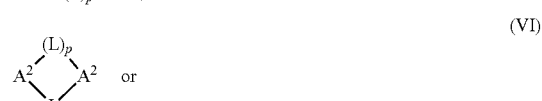

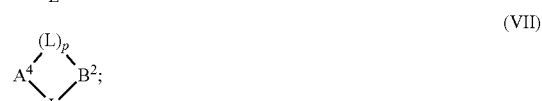

A and B are each phenyl radicals, L=oxygen atom, sulfur atom or alkylene radical and p=0 or 1; processes for their preparation and their use.

3 Claims, No Drawings

METHODS FOR USING CONGENERIC, CHLORINATED, BROMINATED AND/OR IODISED, FLUORINATED AROMATIC STANDARD COMPOUNDS HAVING TWO BENZOL RINGS

CROSS-REFERENCE TO RELATED APPLICATIONS

The present application is a Divisional Application of U.S. patent application Ser. No. 10/589,597, filed May 30, 2007, now abandoned, which is a 371 of International application PCT/EP2005/050779, filed Feb. 16, 2005, which claims priority of DE 10 2004 007 358.9, filed Feb. 16, 2004, the priority of these applications is hereby claimed and these applications are incorporated herein by reference.

BACKGROUND OF THE INVENTION

The present invention relates to novel congeneric, chlorinated, brominated and/or iodinated, fluorinated aromatic compounds having two benzene rings in their base structure.

The present invention also relates to novel processes for preparing congeneric, chlorinated, brominated and/or iodinated, fluorinated aromatic compounds having two benzene rings in their base structure.

The present invention further relates to the use of the novel congeneric, chlorinated, brominated and/or iodinated, fluorinated aromatic compounds having two benzene rings in their base structure.

Polychlorinated diphenyl ethers, biphenyls and diphenylmethanes are still being used as heat transferers, flame-retardant dielectric insulating fluids in high-voltage transformers and capacitors, or as hydraulic oils in mining.

Polybrominated diphenyl ethers and biphenyls are used as flame retardants for plastics. Numerous representatives of these compound classes are, though, highly toxic and/or precursors of highly toxic polychlorinated or polybrominated dibenzofurans or the dibenzo-p-dioxins. Since the compounds are degraded with very great difficulty, if at all, in nature and are also lipophilic, they accumulate in the adipose tissue of organisms and thus also get into the human organism. It is therefore necessary to detect these compounds even only in traces in order to prevent, for example, dangerous contaminations (cf.:

Römpp Online 2003, "Polychlorierte Biphenyle" [Polychlorinated Biphenyls], "PCB-Abbau" [PCB Degradation], "Polybromierte Biphenyle" [Polybrominated Biphenyls], "Schadstoff-Höchstmengen-Verordnung" [German Maximum Harmful Substance Levels Act], "Flammschutzmittel" [Flame Retardants] and "Dioxine" [Dioxins];

Mitchell D. Erickson, "Introduction: PCB Properties, Uses, Occurrence, and Regulatory History", in Roberston and Hanson (Editors), PCB, The University Press of Kentucky, pages xi to xxviii, 2001;

George M. Frame "The Current State-of-the-Art of Comprehensive, Quantitative, Congener-Specific PCB Analysis, and What We Now Know about the Distributions of Individual Congeners in Commercial Aroclor Mixtures", in Robertson and Hanson (Editors), PCB, The University Press of Kentucky, pages 3 to 9, 2001;

Hans-Joachim Lehmler, Carolyn P. Brock, Brian Patrick, Larry D. Robertson, "Synthesis of Polychlorinated Biphenyls (PCBs) and Their Metabolites Using the Suzuki-Coupling", in Robertson and Hanson (Editors), PCB, The University Press of Kentucky, pages 57 to 60, 2001;

Göran Marsh, Jiwei Hu, Eva Jokobsson, Sara Rahm, and Ake Bergman, "Synthesis and Characterization of 32 Polybrominated Diphenyl Ethers", Environmental Science and Technology, volume 33, pages 3033 to 3037, 1999;

Anders Garå, Kurt Andersson, Carl-Axel Nilsson and Ake Norström, "Synthesis of halogenated diphenyl ethers and dibenzofurans—A discussion of specific isomers available", Chemosphere; and Michael Herrmann, Umweltbundesamt, Postfach 33 00 22, 14191 Berlin, Federal Republic of Germany, "UGILEC" August 2002).

The German patent application DE 199 49 950 A1 has already proposed, in quite general terms, the use of chlorinated, brominated and/or iodinated, monofluorinated polycyclic aromatic compounds such as biphenyls, dibenzo-p-dioxins and dibenzofurans as internal standards which, together with their parent compounds, i.e. the unfluorinated chlorinated, brominated and/or iodinated biphenyls, dibenzo-p-dioxins and dibenzofurans, pass through physical, chemical and/or biological processes and are then detected and/or analyzed together with them or separately from them, as external standards which, in place of their parent compounds, pass through physical, chemical and/or biological processes for the purposes of calibrating these processes and are analyzed and/or detected separately from the parent compounds, and/or as model compounds which, in place of their parent compounds, pass through chemical and/or biological processes for the purposes of elucidating the reaction mechanisms and whose reaction products are detected and/or analyzed.

More specific details on the structure of the chlorinated, brominated and/or iodinated, monofluorinated biphenyls, dibenzo-p-dioxins and dibenzofurans and of their preparation are, though, not disclosed. There is no mention of chlorinated, brominated and/or iodinated, monofluorinated diphenyl ethers and diphenylmethanes.

2-Fluoro-4-bromobiphenyl is a commercial product which can be purchased from Synthon. It is suitable only to a limited extent as a standard for the quantitative analysis of chlorinated, brominated and/or iodinated biphenyls.

The Russian patent RU 2091789 C discloses the use of a mixture of monofluorotetrachlorodibenzo-p-dioxin, monofluoro-pentachlorodibenzo-p-dioxin and monofluoroheptachlorodibenzo-p-dioxin as an internal standard for the quantitative analysis of chlorinated dibenzo-p-dioxins. Specifically, 2-fluoro-6,7,8,9-tetrachlorodibenzo-p-dioxin, 2-fluoro-1,3,4,7,8-pentachlorodibenzo-p-dioxin and 2-fluoro-1,3,4,6,7,8,9-heptachlorodibenzo-p-dioxin are used. The mixture is, though, only of limited suitability for the quantitative analysis of chlorinated, brominated and/or iodinated dibenzo-p-dioxins.

Dihalogenated diphenyliodonium salts such as 4,4'-difluoro-, 4,4'-dichloro-, 4,4'-dibromo- and 4,4'-diiododiphenyliodonium salts are known from the article by F. Marshall Beringer, Robert A. Falk, Marilyn Karniol, Irving Lillien, Giulio Masullo, Marvin Mausner and Erwin Sommer "Diaryliodonium Salts. IX. The Synthesis of Substituted Diphenyl Iodonium Salts", Journal of the American Chemical Society, volume 81, pages 342 to 351, 1959. Polybrominated diphenyliodonium salts are known from the article by Göran Marsh, Jiwei Hu, Eva Jokobsson, Sara Rahm, and Ake Bergman, "Synthesis and Characterization of 32 Polybrominated Diphenyl Ethers", Environmental Science and Technology, volume 33, pages 3033 to 3037, 1999. Their use for preparing congeneric, chlorinated, brominated and/or iodinated, monofluorinated diphenyl ethers is not described.

Difluorinated aromatic compounds having at least two benzene rings in their base structure, which are not chlorinated, brominated and/or iodinated, and their use in the analysis of polycyclic aromatic compounds are known from the article by J. T. Anderson and U. Weis, "Gas chromatographic determination of polycyclic aromatic compounds with fluorinated analogues as internal standards", in Journal of Chromatography A, 659 (1994), pages 151 to 161, or the article by G. Luthe, F. Ariese and U. A. Th. Brinkman, "Retention behaviour of higher fluorinated polycyclic aromatic hydrocarbons in reversed-phase liquid chromatography", in Chromatographia, January 2004. It is detailed comprehensively therein that the difluorinated polycyclic aromatic compounds have very much greater differences compared to their parent compounds than the monofluorinated polycyclic aromatic compounds, so that they are less suitable as internal standards.

SUMMARY OF THE INVENTION

It is an object of the present invention to provide novel congeneric, chlorinated, brominated and/or iodinated, fluorinated aromatic compounds having two benzene rings in their base structure, which are advantageously suitable in the analysis of organic compounds, especially environmental analysis, toxicology, biochemistry and medicine,

- as internal standards and surrogate standards which, together with their parent compounds, i.e. the unfluorinated, congeneric, chlorinated, brominated and/or iodinated aromatic compounds with two benzene rings in their base structure, pass through physical, chemical and/or biological processes and are then detected and/or analyzed together with them or separately from them,
- as external standards which, in place of their parent compounds, pass through physical, chemical and/or biological processes for the purposes of calibrating these processes and are analyzed and/or detected separately from the parent compounds, and/or
- as model compounds which, in place of their parent compounds, pass through chemical and/or biological processes for the purposes of elucidating the reaction mechanisms and whose reaction products are detected and/or analyzed, or can be used advantageously as valuable intermediates for preparing chlorinated, brominated and/or iodinated, monofluorinated or difluorinated aromatic compounds having two benzene rings in their base structure.

It is also an object of the present invention to provide novel processes for preparing congeneric, chlorinated, brominated and/or iodinated, fluorinated aromatic compounds having two benzene rings in their base structure, which permit the controlled preparation of these novel compounds in a simple manner.

THE INVENTIVE SOLUTION

Accordingly, the novel congeneric, chlorinated, brominated and/or iodinated, fluorinated aromatic compounds having two benzene rings in their base structure have been found, the fluorinated aromatic compounds having the general formula I or II:

where the index and the variables are each defined as follows:

p is 0 or 1;

$A^1$ is a monovalent, monofluorinated phenyl radical or monovalent, chlorinated, brominated and/or iodinated, monofluorinated phenyl radical;

$B^1$ is a monovalent, chlorinated, brominated and/or iodinated phenyl radical or monovalent, unhalogenated phenyl radical;

$A^2$ is a divalent, monofluorinated phenyl radical or divalent, chlorinated, brominated and/or iodinated, monofluorinated phenyl radical;

$B^2$ is a divalent, chlorinated, brominated and/or iodinated phenyl radical or divalent, unhalogenated phenyl radical;

L is an oxygen atom, sulfur atom or alkylene radical;

with the provisos that (1) in the compounds I and II, the phenyl radical $A^1$ or $A^2$ is chlorinated, brominated and/or iodinated when the phenyl radical $B^1$ or $B^2$ is unhalogenated;

(2) in the monobrominated compounds I where p=0, the phenyl radical $B^1$ is substituted by the bromine atom;

(3) in the tetrachlorinated compounds II where p=1 and L=oxygen atom, both phenyl radicals $A^2$ and $B^2$ are substituted by at least one chlorine atom and (4) the penta-, hexa- and heptahalogenated compounds II where p=1 and L=oxygen atom are substituted by bromine and/or iodine or by chlorine and bromine and/or iodine;

or have the general formula III, IV, V, VI or VII:

where the variables $A^1$, $B^1$, $A^2$, $B^2$ and L and the index p are each as defined above and the variables Y, $A^3$ and $A^4$ and the index q are each defined as follows:

q is an integer from 1 to 4;

Y is an acid anion;

$A^3$ is a monovalent, difluorinated phenyl radical or monovalent, chlorinated, brominated and/or iodinated, difluorinated phenyl radical;

$A^4$ is a divalent, difluorinated phenyl radical or divalent, chlorinated, brominated and/or iodinated, difluorinated phenyl radical;

with the provisos that (5) in the difluorinated compounds III, $A^1$ is not a monovalent, monofluorinated phenyl radical;

(6) in the difluorinated compounds IV, at least one phenyl radical $A^1$ is chlorinated, brominated and/or iodinated;

(7) in the difluorinated compounds V, the phenyl radical $A^3$ is chlorinated, brominated and/or iodinated when the monovalent phenyl radical $B^1$ is not halogenated;

(8) in the difluorinated compounds VI, at least one phenyl radical $A^2$ is chlorinated, brominated and/or iodinated and (9) in the difluorinated compounds VII, the phenyl radical $A^3$ is chlorinated, brominated and/or iodinated when the divalent phenyl radical $B^2$ is not halogenated.

The novel congeneric, chlorinated, brominated and/or iodinated, fluorinated aromatic compounds having two benzene rings in their base structure of the general formula I to VII will be referred to hereinafter as "inventive compounds I to VII".

Additionally found has been the novel process for preparing inventive compounds I, IV or V, in which (1) a symmetrical difluorinated or tetrafluorinated iodonium salt of the general formula (VIII):

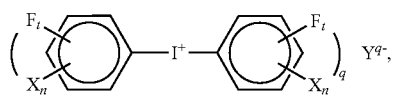
(VIII)

where the index and the variables are each defined as follows:
t is 1 or 2,
n is 0 or an integer from 1 to 4,
q is an integer from 1 to 4,
X is chlorine, bromine and/or iodine and
Y is an acid anion;

is reacted with a chlorinated, brominated and/or iodinated phenol of the general formula (IX):

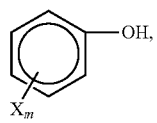
(IX)

where the index m=0 or an integer from 1 to 5 and the variable X is as defined above;
with the proviso that m=an integer from 1 to 5 when n=0;
or, alternatively, (2) a symmetrical unfluorinated diphenyliodonium salt of the general formula (X):

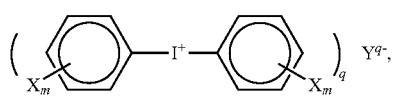
(X)

where the variables X and Y and the indices m and q are each as defined above;

is reacted with a monofluorinated or difluorinated phenol of the general formula (XI):

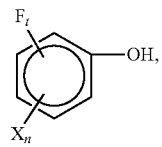
(XI)

where the index n and the variable X are each as defined above and the index t=1 or 2;
with the provisos that m=an integer from 1 to 5 when n=0, and n=an integer from 1 to 4 when m=0.

The novel process for preparing inventive compounds I, IV or V is referred to hereinafter as "inventive process I".

Also found has been the novel process for preparing inventive compounds I, II and IV to VII, in which (1) a chlorinated, brominated and/or iodinated aromatic compound having two benzene rings in its base structure of the general formula XII or XIII:

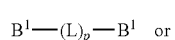
(XII)

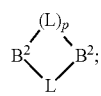
(XIII)

where the variables $B^1$, $B^2$ and L and the index p are each as defined above, with the proviso that at least one of the phenyl radicals $B^1$ or $B^2$ is chlorinated, brominated and/or iodinated; is monofluorinated or difluorinated, or, alternatively, (2) a monofluorinated or difluorinated, aromatic compound having two benzene rings in its base structure of the general formula XIV to XIX:

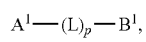
(XIV)

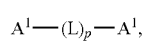
(XV)

(XVI)

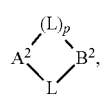
(XVII)

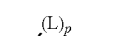
(XVIII)

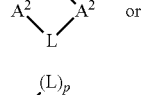

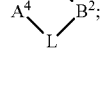
(XIX)

where the indices and the variables are each as defined above, with the proviso that the phenyl radicals $A^1$ to $A^4$ and $B^1$ and $B^2$ are not chlorinated, brominated or iodinated, are chlorinated, brominated and/or iodinated, or, alternatively, (3) a chlorinated, brominated and/or iodinated benzene derivative is reacted with a brominated and/or iodinated, monofluorinated or difluorinated benzene or alkylbenzene or a brominated and/or iodinated, chlorinated, monofluorinated or difluorinated benzene or alkylbenzene, or, alternatively, (4) a chlorinated, brominated and/or iodinated, monofluorinated or difluorinated benzene derivative is reacted with a brominated and/or iodinated benzene or alkylbenzene or a brominated and/or iodinated, chlorinated benzene or alkylbenzene.

The novel process for preparing inventive compounds I, II or IV to VII will be referred to hereinafter as "inventive process 2".

Moreover, the novel process for preparing inventive compounds III has been found, in which a chlorinated, brominated and/or iodinated, monofluorinated or difluorinated benzene is reacted with iodyl sulfate and which is referred to hereinafter as "inventive process 3".

Not least, the novel use of the inventive compounds I to VIII and of the inventive compounds I to VII prepared by the inventive processes 1 to 3 in the analysis and the synthesis of organic compounds has been found, which is referred to hereinafter comprehensively as "inventive use".

Further subject matter of the invention is evident from the description.

THE ADVANTAGES OF THE INVENTIVE SOLUTION

In view of the prior art, it was surprising and unforeseeable to the person skilled in the art that the problem underlying the present invention could be solved with the aid of the inventive compounds I to VIII, the inventive processes 1, 2 and 3 and the inventive use.

In particular, it was surprising that the inventive compounds I, II and IV to VII were usable in an outstandingly advantageous manner in the analysis of organic compounds, especially environmental analysis, toxicology, biochemistry and medicine,

- as internal standards or surrogate standards which, together with their parent compounds, i.e. the unfluorinated, congeneric, chlorinated, brominated and/or iodinated aromatic compounds with two benzene rings in their base structure, pass through physical, chemical and/or biological processes and are then detected and/or analyzed together with them or separately from them,
- as external standards which, in place of their parent compounds, pass through physical, chemical and/or biological processes for the purposes of calibrating these processes and are analyzed and/or detected separately from the parent compounds, and/or
- as model compounds which, in place of their parent compounds, pass through chemical and/or biological processes for the purposes of elucidating the reaction mechanisms and whose reaction products are detected and/or analyzed.

Moreover, it was surprising that the inventive compounds I, IV or V were preparable in a simple, elegant and very reproducible manner with the aid of the inventive process 1.

In addition, it was surprising that the inventive compounds I, II and IV to VII were preparable in a simple, elegant and very reproducible manner with the aid of the inventive process 2.

Furthermore, it was surprising that the inventive compounds III were preparable in a simple, elegant and very reproducible manner with the aid of the inventive process 3.

DETAILED DESCRIPTION OF THE INVENTION

1. The Inventive Compounds I to VII 1.1 Preliminary Remark

In the context of the present invention, the passage "having two benzene rings in their base structure" means that the inventive compounds I to VII have a base structure with two base benzene rings which are bonded to one another directly, i.e. via a carbon-carbon bond and/or via at least one oxygen atom, sulfur atom and/or at least one alkylene radical and may be substituted by further aromatic radicals and/or fused. These further aromatic radicals may likewise be chlorinated, brominated and/or iodinated. Moreover, both the base structure and any further aromatic radicals present may also bear other substituents other than aromatic radicals and halogen atoms. Examples of suitable other substituents are optionally fluorinated, chlorinated, brominated and/or iodinated alkyl groups, especially methyl groups. The base structure preferably has no further aromatic radicals.

1.2 The Inventive Compounds I

The inventive compounds I have the general formula I

$$A^1\text{-}(L)_p\text{-}B^1 \tag{I}$$

In the general formula, the variables and the index are defined as follows:

p is 0 or 1;

$A^1$ is a monofluorinated phenyl radical or chlorinated, brominated and/or iodinated, especially chlorinated and/or brominated, monofluorinated phenyl radical;

$B^1$ is a chlorinated, brominated and/or iodinated, especially chlorinated and/or brominated, phenyl radical or unhalogenated phenyl radical and L is an oxygen atom, sulfur atom or alkylene radical, preferably oxygen atom or alkylene radical and especially oxygen atom and methylene radical;

with the provisos that (1) in the compounds I, the phenyl radical $A^1$ is chlorinated, brominated and/or iodinated when the phenyl radical $B^1$ is unhalogenated and (2) in the monobrominated compounds I where p=0, the phenyl radical $B^1$ is substituted by the bromine atom.

In the case that p=0, the phenyl radicals $A^1$ and $B^1$ are joined by a carbon-carbon single bond.

In particular, the inventive compounds I are biphenyls I, diphenyl ethers I and diphenylmethanes I.

The phenyl radical $A^1$ preferably has the general formula XX:

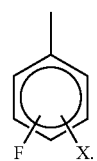

(XX)

In the general formula XX, the variable X represents halogen atoms selected from the group consisting of chlorine, bromine and iodine, preferably chlorine and bromine. The index n=0 or an integer from 1 to 4.

The phenyl radical B¹ preferably has the general formula XXI:

$$\text{(XXI)}$$

[Structure: phenyl ring with X$_m$ substituent]

In the general formula XXI, the variable X represents halogen atoms selected from the group consisting of chlorine, bromine and iodine, preferably chlorine and bromine. The index m=0 or an integer from 1 to 5.

The phenyl radical A¹ is preferably selected from the group consisting of:
2-, 3- and 4-fluorophenyl;
2-fluoro-3-halo-, 2-fluoro-4-halo-, 2-fluoro-5-halo- and 2-fluoro-6-halophenyl;
3-fluoro-2-halo-, 3-fluoro-4-halo-, 3-fluoro-5-halo- and 3-fluoro-6-halophenyl;
4-fluoro-2-halo- and 4-fluoro-3-halophenyl;
2-fluoro-3,4-dihalo-, 2-fluoro-3,5-dihalo-, 2-fluoro-3,6-dihalo-, 2-fluoro-4,5-dihalo- and 2-fluoro-4,6-dihalophenyl;
3-fluoro-2,4-dihalo-, 3-fluoro-2,5-dihalo-, 3-fluoro-2,6-dihalo-, 3-fluoro-4,5-dihalo, 3-fluoro-4,6-dihalo- and 3-fluoro-5,6-dihalophenyl;
4-fluoro-2,3-dihalo-, 4-fluoro-2,5-dihalo-, 4-fluoro-3,5-dihalo- and 4-fluoro-2,6-dihalophenyl;
2-fluoro-3,4,5-trihalo-, 2-fluoro-3,4,6-trihalo- and 2-fluoro-4,5,6-trihalophenyl;
3-fluoro-2,4,5-trihalo-, 3-fluoro-2,4,6-trihalo- and 3-fluoro-4,5,6-trihalophenyl;
4-fluoro-2,3,5-trihalo- and 4-fluoro-2,5,6-trihalophenyl; and
2-fluoro-3,4,5,6-tetrahalo-, 3-fluoro-2,4,5,6-tetrahalo- and 4-fluoro-2,3,5,6-tetrahalophenyl;
where the halogen is selected from the group consisting of chlorine, bromine and iodine, preferably chlorine and bromine.

In particular, the phenyl radical A¹ is selected from the group consisting of:
2-, 3- and 4-fluorophenyl;
2-fluoro-4-chloro-3-bromo-, 2 fluoro-3-chloro-4-bromo-, 2-fluoro-5-chloro-3-bromo-, 2-fluoro-3-chloro-5-bromo-, 2-fluoro-6-chloro-3-bromo-, 2-fluoro-3-chloro-6-bromo-, 2-fluoro-5-chloro-4-bromo-, 2-fluoro-4-chloro-5-bromo-, 2-fluoro-6-chloro-4-bromo-, 2-fluoro-4-chloro-6-bromo-, 2-fluoro-5-chloro-6-bromo- and 2-fluoro-6-chloro-5-bromophenyl;
3-fluoro-4-chloro-2-bromo-, 3-fluoro-2-chloro-4-bromo-, 3-fluoro-5-chloro-2-bromo-, 3-fluoro-2-chloro-5-bromo-, 3-fluoro-6-chloro-2-bromo-, 3-fluoro-2-chloro-6-bromo-, 3-fluoro-5-chloro-4-bromo-, 3-fluoro-4-chloro-5-bromo-, 2-fluoro-6-chloro-4-bromo-, 3-fluoro-4-chloro-6-bromo-, 3-fluoro-6-chloro-5-bromo- and 3-fluoro-5-chloro-6-bromophenyl;
4-fluoro-3-chloro-2-bromo-, 4-fluoro-2-chloro-3-bromo-, 4-fluoro-2-chloro-5-bromo-, 4-fluoro-5-chloro-3-bromo- and 4-fluoro-2-chloro-6-bromophenyl;
2-fluoro-4,5-dichloro-3-bromo-, 2-fluoro-3,5-dichloro-4-bromo-, 2-fluoro-3,4-dichloro-5-bromo-, 2-fluoro-5-chloro-3,4-dibromo-, 2-fluoro-4-chloro-3,5-dibromo-, 2-fluoro-3-chloro-4,5-dibromo-, 2-fluoro-3,4-dichloro-3-bromo-, 2-fluoro-3,6-dichloro-4-bromo-, 2-fluoro-3,4-dichloro-6-bromo-, 2-fluoro-6-chloro-3,4-dibromo-, 2-fluoro-4-chloro-3,6-dibromo-, 2-fluoro-3-chloro-4,6-dibromo-, 2-fluoro-5,6-dichloro-4-bromo-, 2-fluoro-4,6-dichloro-5-bromo-, 2-fluoro-4,5-dichloro-6-bromo-, 2-fluoro-6-chloro-4,5-dibromo-, 2-fluoro-5-chloro-4,6-dibromo-, 2-fluoro-4-chloro-5,6-dibromo- and 2-fluoro-4-chloro-5,6-dibromophenyl;
3-fluoro-4,5-dichloro-2-bromo-, 3-fluoro-2,5-dichloro-4-bromo-, 3-fluoro-2,4-dichloro-5-bromo-, 3-fluoro-4-chloro-2,5-dibromo-, 3-fluoro-2-chloro-4,5-dibromo-, 3-fluoro-5-chloro-2,4-dibromo-, 3-fluoro-4,6-dichloro-2-bromo-, 3-fluoro-2,6-dichloro-4-bromo-, 3-fluoro-6-chloro-2,4-dibromo-, 3-fluoro-4-chloro-2,6-dibromo-, 3-fluoro-2-chloro-4,6-dibromo-, 3-fluoro-5,6-dichloro-4-bromo-, 3-fluoro-4,6-dichloro-5-bromo-, 3-fluoro-4,5-dichloro-6-bromo-, 3-fluoro-6-chloro-4,5-dibromo-, 3-fluoro-4-chloro-5,6-dibromo- and 3-fluoro-5-chloro-4,6-dibromophenyl;
4-fluoro-2,3-dichloro-5-bromo-, 4-fluoro-2,5-dichloro-3-bromo-, 4-fluoro-3,5-dichloro-2-bromo-, 4-fluoro-3-chloro-5,6-dibromo-, 4-fluoro-3-chloro-2,5-dibromo-, 4-fluoro-2-chloro-3,5-dibromo-, 4-fluoro-2,3-dichloro-6-bromo-, 4-fluoro-2,6-dichloro-3-bromo-, 4-fluoro-2,5-dichloro-6-bromo-, 4-fluoro-2-chloro-5,6-dibromo-, 4-fluoro-2-chloro-3,6-dibromo- and 4-fluoro-3-chloro-2,6-dibromophenyl;
2-fluoro-4,5,6-trichloro-3-bromo-, 2-fluoro-3,5,6-trichloro-4-bromo-, 2-fluoro-3,4,6-trichloro-5-bromo-, 2-fluoro-3,4,5-trichloro-6-bromo-, 2-fluoro-5,6-dichloro-3,4-dibromo-, 2-fluoro-4,6-dichloro-3,5-dibromo-, 2-fluoro-4,5-dichloro-3,6-dibromo-, 2-fluoro-3,6-dichloro-4,5-dibromo-, 2-fluoro-3,5-dichloro-4,6-dibromo-, 2-fluoro-3,4-dichloro-5,6-dibromo-, 2-fluoro-3-chloro-4,5,6-tribromo-, 2-fluoro-4-chloro-3,5,6-tribromo-, 2-fluoro-5-chloro-3,4,6-tribromo- and 2-fluoro-6-chloro-3,4,5-tribromophenyl;
3-fluoro-4,5,6-trichloro-2-bromo-, 3-fluoro-2,5,6-trichloro-4-bromo-, 3-fluoro-2,4,6-trichloro-5-bromo-, 3-fluoro-2,4,5-trichloro-6-bromo-, 3-fluoro-5,6-dichloro-2,4-dibromo-, 3-fluoro-4,6-dichloro-2,5-dibromo-, 3-fluoro-4,5-dichloro-2,6-dibromo-, 3-fluoro-2,4-dichloro-5,6-dibromo-, 3-fluoro-2,5-dichloro-4,6-dibromo-, 3-fluoro-2,6-dichloro-4,5-dibromo-, 3-fluoro-6-chloro-2,4,5-tribromo-, 3-fluoro-5-chloro-2,4,6-tribromo-, 3-fluoro-4-chloro-2,5,6-tribromo- and 3-fluoro-2-chloro-4,5,6-tribromophenyl; and
4-fluoro-2,3,5-trichloro-6-bromo-, 4-fluoro-2,3,6-trichloro-5-bromo-, 4-fluoro-2,3-dichloro-5,6-dibromo-, 4-fluoro-2,6-dichloro-3,5-dibromo-, 4-fluoro-3,5-dichloro-2,6-dibromo-, 4-fluoro-2,5-dichloro-3,6-dibromo-, 4-fluoro-2-chloro-3,5,6-tribromo- and 4-fluoro-3-chloro-2,5,6-tribromophenyl.

The phenyl radical B¹ is preferably selected from the group consisting of:
phenyl;
2-, 3- and 4-halophenyl;
2,3-, 2,4-, 2,5-, 2,6-, 3,4- and 3,5-dihalophenyl;
2,3,4-, 2,4,5-, 2,4,6- and 3,4,5-trihalophenyl;
2,3,4,6- and 2,3,4,5-tetrahalophenyl; and
pentahalophenyl;
where the halogen is selected from the group consisting of chlorine, bromine and iodine, preferably chlorine and bromine.

In particular, the phenyl radical B¹ is selected from the group consisting of:
2-chloro-6-bromo-, 3-chloro-2-bromo-, 2-chloro-3-bromo-, 2-chloro-5-bromo-, 3-chloro-6-bromo-, 4-chloro-2-bromo- and 2-chloro-4-bromophenyl;

2,4-dichloro-6-bromo-, 2,6-dichloro-4-bromo-, 4-chloro-2, 6-dibromo-, 2-chloro-4,6-dibromo-, 2,3-dichloro-4-bromo-, 2,4-dichloro-3-bromo-, 3,4-dichloro-2-bromo-, 4-chloro-2,3-dibromo-, 3-chloro-2,4-dibromo-, 2-chloro-3,4-dibromo-, 3,4-dichloro-5-bromo-, 3,5-dichloro-4-bromo-, 3-chloro-4,5-dibromo- and 4-chloro-3,5-dibromophenyl;

2,4,5-trichloro-6-bromo-, 2,4,6-trichloro-3-bromo-, 2,3,6-trichloro-4-bromo-, 2,3,4-trichloro-5-bromo- and 2,3,4-trichloro-6-bromo-, 2,4-dichloro-5,6-dibromo-, 2,5-dichloro-4,6-dibromo-, 3,4-dichloro-2,6-dibromo-, 2,6-dichloro-3,4-dibromo-, 2,4-dichloro-3,6-dibromo-, 2-chloro-4,5,6-tribromo-, 3-chloro-4,5,6-tribromo-, 4-chloro-2,5,6-tribromo-, 4-chloro-3,5,6-tribromo-, 3-chloro-2,4,6-tribromo- and 2-chloro-3,4,6-tribromophenyl; and 2,3,4,5-tetrachloro-6-bromo-, 2,3,4,6-tetrachloro-5-bromo-, 2,3,5,6-tetrachloro-4-bromo-, 2,2,4-trichloro-5,6-dibromo-, 2,4,5-trichloro-3,6-dibromo-, 3,4,5-trichloro-2,6-dibromo-, 2,3-dichloro-4,5,6-tribromo-, 2,4-dichloro-3,5,6-tribromo-, 2,5-dichloro-3,4,6-tribromo-, 2,6-dichloro-3,4,5-tribromo-, 2-chloro-3,4,5,6-tetrabromo-, 3-chloro-2,4,5,6-tetrabromo- and 4-chloro-2,3,5,6-tetrabromophenyl.

The inventive biphenyls I and diphenyl ethers I preferably contain no other substituents. The inventive diphenylmethanes I preferably contain at least one other substituent, especially a methyl group.

Taking account of the inventive provisos, all of the above-described phenyl radicals $A^1$ and $B^1$ can be combined with one another to give the inventive diphenyl ethers I, biphenyls and diphenylmethanes I. Examples of combinations, i.e. inventive diphenyl ethers I, diphenylmethanes I and biphenyls I, are 4'-fluoro-2,3',4-tribromodiphenyl ether,
4'-fluoro-2,3',6-tribromodiphenyl ether,
4'-fluoro-2,3',4,6-tetrabromodiphenyl ether,
4'-fluoro-2,3,3',4,5,6-hexabromodiphenyl ether,
3'-fluoro-2,4,4'-trichlorobiphenyl or
4-methyl-2,2',5,6-tetrachloro-3'-fluorodiphenylmethane.

1.3 The Inventive Compounds II

The inventive compounds II have the general formula II:

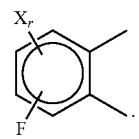

(II)

In the general formula II, the index p and the variable L are each as defined above.

The variable $A^2$ represents a divalent monofluorinated phenyl radical or a chlorinated, brominated and/or iodinated, divalent, monofluorinated phenyl radical.

The variable $B^2$ represents a chlorinated, brominated and/or iodinated phenyl radical or an unhalogenated divalent phenyl radical.

The following provisos should be taken into account:
(1) In the inventive compounds II, the phenyl radical $A^2$ is chlorinated, brominated and/or iodinated when the phenyl radical $B^2$ is unhalogenated.
(3) In the tetrachlorinated inventive compounds II where p=1 and L=oxygen atom, both phenyl radicals $A^2$ and $B^2$ are substituted by at least one chlorine atom.
(4) The penta-, hexa- and heptahalogenated inventive compounds II where p=1 and L=oxygen atom are substituted by bromine and/or iodine or by chlorine and bromine and/or iodine.

In the case that p=0, the phenyl radicals $A^2$ and $B^2$ are joined by a carbon-carbon single bond.

In particular, the inventive compounds II are dibenzo-p-dioxins II and dibenzofurans II.

The phenyl radical $A^2$ preferably has the general formula XXII:

(XXII)

In the general formula XXII, the variable X represents halogen atoms selected from the group consisting of chlorine, bromine and iodine, preferably chlorine and bromine. The index r=0 or an integer >from 1 to 3.

The phenyl radical $A^2$ is preferably selected from the group consisting of
3-fluorophen-1,2-ylene;
3-fluoro-4-chloro- and -4-bromphen-1,2-ylene;
3-fluoro-4,5-dichloro-, -4,5-dibromo-, -4-chloro-5-bromo- and -4-bromo-5-chlorophen-1,2-ylene;
3-fluoro-4,5,6-trichloro-, -4,5,6-tribromo-, -4-chloro-5,6-dibromo-, -5-chloro-4,6-dibromo-, -4-bromo-5,6-dichloro- and -5-bromo-4,6-dichlorophen-1,2-ylene;
4-fluorophen-1,2-ylene;
4-fluoro-3-chloro- and -3-bromophen-1,2-ylene;
4-fluoro-5-chloro- and -5-bromophen-1,2-ylene;
4-fluoro-6-chloro- and -6-bromophen-1,2-ylene;
4-fluoro-3,5-dichloro-, -3,5-dibromo-, -3-chloro-5-bromo- and -3-bromo-5-chlorophen-1,2-ylene;
4-fluoro-3,6-dichloro-, -3,6-dibromo-, -3-chloro-6-bromo- and -3-bromo-6-chlorophen-1,2-ylene;
4-fluoro-5,6-dichloro-, -5,6-dibromo-, -5-chloro-6-bromo- and -5-bromo-6-chlorophen-1,2-ylene; and
4-fluoro-3,5,6-trichloro-, -3,5,6-tribromo-, -3-chloro-5,6-tribromo-, -3-bromo-5,6-dichloro-, -5-chloro-3,6-dibromo-, -5-bromo-3,6-dichloro-, 6-chloro-3,6-dibromo- and -6-bromo-3,6-dichlorophen-1,2-ylene.

In particular, they are selected from the group consisting of 3-fluoro-4,5-dichlorophen-1,2-ylene, 4-fluoro-3,5-dichlorophen-1,2-ylene and 3-fluoro-4,5,6-trichlorophen-1,2-ylene.

The phenyl radical $B^2$ preferably has the general formula XXIII

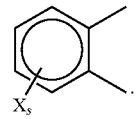

(XXIII)

In the general formula XXIII, the variable X represents halogen atoms selected from the group consisting of chlorine, bromine and iodine, preferably chlorine and bromine. The index s=0 or an integer from 1 to 4.

The phenyl radical $B^2$ is preferably selected from the group consisting of
phen-1,2-ylene;
3-chloro- and 3-bromophen-1,2-ylene;
4-chloro- and 4-bromophen-1,2-ylene;

3,4-dichloro-, 3,4-dibromo-, 3-chloro-4-bromo- and 3-bromo-4-chlorophen-1,2-ylene;
3,5-dichloro-, 3,5-dibromo-, 3-chloro-5-bromo- and 3 bromo-5-chlorophen-1,2-ylene;
4,5-dichloro-, 4,5-dibromo- and 4-chloro-5-bromophen-1,2-ylene;
3,4,5-trichloro-, 3,4,5-tribromo-, 3-chloro-4,5-dibromo-, 3-bromo-4,5-dichloro-, 4-chloro-3,5-dibromo- and 4-bromo-3,5-dichlorophen-1,2-ylene;
3,4,6-trichloro-, 3,4,6-tribromo-, 3-chloro-4,6-dibromo-, 4-chloro-3,6-dibromo- and 4-bromo-3,6-dichlorophen-1, 2-ylene; and
3,4,5,6-tetrachloro-, 3,4,5,6-tetrabromo-, 3-chloro-4,5,6-tribromo-, 3-bromo-4,5,6-trichloro-, 3,4-dichloro-5,6-dibromo-, 3,5-dichloro-4,6-dibromo-, 4,5-dichloro-3,6-dibromo- and 4,5-dibromo-3,6-dichlorophen-1,2-ylene.

In particular, the phenyl radical $B^2$ is 4,5-dichlorophen-1,2-ylene or 3,4,5,6-tetrachlorophen-1,2-ylene.

The inventive dibenzo-p-dioxins II and dibenzofurans II preferably contain no other substituents.

Taking account of the inventive provisos, all of the above-described phenyl radicals $A^2$ and $B^2$ may be combined with one another to give the inventive dibenzo-p-dioxins II and dibenzofurans II. Examples of such combinations, i.e. inventive dibenzo-p-dioxins II and dibenzofurans II, are
1-fluoro-2,3,7,8-tetrachlorodibenzo-p-dioxin,
2-fluoro-1,4,6,9-tetrachlorodibenzo-p-dioxin and
4-fluoro-1,3,6,7,8,9-hexachlorodibenzofuran.

1.4 The Inventive Compounds III

The inventive compounds III have the general formula III:

  (IIIa) or

  (IIIb).

In the general formula IIIa, the variable $A^1$ is as defined above excluding a monofluorinated phenyl radical. The variable Y is an acid anion, preferably $Cl^-$ and $SO_4^{2-}$. The index q is an integer from 1 to 4, especially 1 and 2.

The phenyl radical $A^1$ in the general formula IIIa preferably has the general formula XX as described above, where n=an integer from 1 to 4.

Accordingly, the phenyl radical $A^1$ is preferably selected from the group consisting of:
2-fluoro-3-halo-, 2-fluoro-4-halo-, 2-fluoro-5-halo- and 2-fluoro-6-halophenyl;
3-fluoro-2-halo-, 3-fluoro-4-halo-, 3-fluoro-5-halo- and 3-fluoro-6-halophenyl;
4-fluoro-2-halo- and 4-fluoro-3-halophenyl;
2-fluoro-3,4-dihalo-, 2-fluoro-3,5-dihalo-, 2-fluoro-3,6-dihalo-, 2-fluoro-4,5-dihalo- and 2-fluoro-4,6-dihalophenyl;
3-fluoro-2,4-dihalo-, 3-fluoro-2,5-dihalo-, 3-fluoro-2,6-dihalo-, 3-fluoro-4,5-dihalo-, 3-fluoro-4,6-dihalo- and 3-fluoro-5,6-dihalophenyl;
4-fluoro-2,3-dihalo-, 4-fluoro-2,5-dihalo-, 4-fluoro-3,5-dihalo- and 4-fluoro-2,6-dihalophenyl;
2-fluoro-3,4,5-trihalo-, 2-fluoro-3,4,6-trihalo- and 2-fluoro-4,5,6-trihalophenyl;
3-fluoro-2,4,5-trihalo-, 3-fluoro-2,4,6-trihalo- and 3-fluoro-4,5,6-trihalophenyl;
4-fluoro-2,3,5-trihalo- and 4-fluoro-2,5,6-trihalophenyl; and
2-fluoro-3,4,5,6-tetrahalo-, 3-fluoro-2,4,5,6-tetrahalo- and 4-fluoro-2,3,5,6-tetrahalophenyl;
where the halogen is selected from the group consisting of chlorine, bromine and iodine, preferably chlorine and bromine.

In particular, the phenyl radical $A^1$ is selected from the group consisting of:
2-fluoro-4-chloro-3-bromo-, 2-fluoro-3-chloro-4-bromo-, 2-fluoro-5-chloro-3-bromo-, 2-fluoro-3-chloro-5-bromo-, 2-fluoro-6-chloro-3-bromo-, 2-fluoro-3-chloro-6-bromo-, 2-fluoro-5-chloro-4-bromo-, 2-fluoro-4-chloro-5-bromo-, 2-fluoro-6-chloro-4-bromo-, 2-fluoro-4-chloro-6-bromo-, 2-fluoro-5-chloro-6-bromo- and 2-fluoro-6-chloro-5-bromophenyl;
3-fluoro-4-chloro-2-bromo-, 3-fluoro-2-chloro-4-bromo-, 3-fluoro-5-chloro-2-bromo-, 3-fluoro-2-chloro-5-bromo-, 3-fluoro-6-chloro-2-bromo-, 3-fluoro-2-chloro-6-bromo-, 3-fluoro-5-chloro-4-bromo-, 3-fluoro-4-chloro-5-bromo-, 2-fluoro-6-chloro-4-bromo-, 3-fluoro-4-chloro-6-bromo-, 3-fluoro-6-chloro-5-bromo- and 3-fluoro-5-chloro-6-bromophenyl;
4-fluoro-3-chloro-2-bromo-, 4-fluoro-2-chloro-3-bromo-, 4-fluoro-2-chloro-5-bromo-, 4-fluoro-5-chloro-3-bromo- and 4-fluoro-2-chloro-6-bromophenyl;
2-fluoro-4,5-dichloro-3-bromo-, 2-fluoro-3,5-dichloro-4-bromo-, 2-fluoro-3,4-dichloro-5-bromo-, 2-fluoro-5-chloro-3,4-dibromo-, 2-fluoro-4-chloro-3,5-dibromo-, 2-fluoro-3-chloro-4,5-dibromo-, 2-fluoro-3,4-dichloro-3-bromo-, 2-fluoro-3,6-dichloro-4-bromo-, 2-fluoro-3,4-dichloro-6-bromo-, 2-fluoro-6-chloro-3,4-dibromo-, 2-fluoro-4-chloro-3,6-dibromo-, 2-fluoro-3-chloro-4,6-dibromo-, 2-fluoro-5,6-dichloro-4-bromo-, 2-fluoro-4,6-dichloro-5-bromo-, 2-fluoro-4,5-dichloro-6-bromo-, 2-fluoro-6-chloro-4,5-dibromo-, 2-fluoro-5-chloro-4,6-dibromo- and 2-fluoro-4-chloro-5,6-dibromophenyl;
3-fluoro-4,5-dichloro-2-bromo-, 3-fluoro-2,5-dichloro-4-bromo-, 3-fluoro-2,4-dichloro-5-bromo-, 3-fluoro-4-chloro-2,5-dibromo-, 3-fluoro-2-chloro-4,5-dibromo-, 3-fluoro-5-chloro-2,4-dibromo-, 3-fluoro-4,6-dichloro-2-bromo-, 3-fluoro-2,6-dichloro-4-bromo-, 3-fluoro-6-chloro-2,4-dibromo-, 3-fluoro-4-chloro-2,6-dibromo-, 3-fluoro-2-chloro-4,6-dibromo-, 3-fluoro-5,6-dichloro-4-bromo-, 3-fluoro-4,6-dichloro-5-bromo-, 3-fluoro-4,5-dichloro-6-bromo-, 3-fluoro-6-chloro-4,5-dibromo-, 3-fluoro-4-chloro-5,6-dibromo- and 3-fluoro-5-chloro-4,6-dibromophenyl;
4-fluoro-2,3-dichloro-5-bromo-, 4-fluoro-2,5-dichloro-3-bromo-, 4-fluoro-3,5-dichloro-2-bromo-, 4-fluoro-3-chloro-5,6-dibromo-, 4-fluoro-3-chloro-2,5-dibromo-, 4-fluoro-2-chloro-3,5-dibromo-, 4-fluoro-2,3-dichloro-6-bromo-, 4-fluoro-2,6-dichloro-3-bromo-, 4-fluoro-2,5-dichloro-6-bromo, 4-fluoro-2-chloro-5,6-dibromo-, 4-fluoro-2-chloro-3,6-dibromo- and 4-fluoro-3-chloro-2,6-dibromophenyl;
2-fluoro-4,5,6-trichloro-3-bromo-, 2-fluoro-3,5,6-trichloro-4-bromo-, 2-fluoro-3,4,6-trichloro-5-bromo-, 2-fluoro-3,4,5-trichloro-6-bromo-, 2-fluoro-5,6-dichloro-3,4-dibromo-, 2-fluoro-4,6-dichloro-3,5-dibromo-, 2-fluoro-4,5-dichloro-3,6-dibromo-, 2-fluoro-3,6-dichloro-4,5-dibromo-, 2-fluoro-3,5-dichloro-4,6-dibromo-, 2-fluoro-3,4-dichloro-5,6-dibromo-, 2-fluoro-3-chloro-4,5,6-tribromo-, 2-fluoro-4-chloro-3,5,6-tribromo-, 2-fluoro-5-chloro-3,4,6-tribromo- and 2-fluoro-6-chloro-3,4,5-tribromophenyl;
3-fluoro-4,5,6-trichloro-2-bromo-, 3-fluoro-2,5,6-trichloro-4-bromo-, 3-fluoro-2,4,6-trichloro-5-bromo-, 3-fluoro-2,4,5-trichloro-6-bromo-, 3-fluoro-5,6-dichloro-2,4-dibromo-, 3-fluoro-4,6-dichloro-2,5-dibromo-, 3-fluoro-2,4-dichloro-5,6-dibromo-, 3-fluoro-2,6-dichloro-2,6-dibromo-, 3-fluoro-2,4-dichloro-5,6-dibromo-, 3-fluoro-2,5-dichloro-4,6-dibromo-, 3-fluoro-2,6-dichloro-4,5-dibromo-, 3-fluoro-6-chloro-2,4,5- tribromo-, 3-fluoro-5-chloro-2,4,6-tribromo-, 3-fluoro-4-chloro-2,5,6-tribromo- and 3-fluoro-2-chloro-4,5,6-tribromophenyl; and 4-fluoro-2,3,5-trichloro-6-bromo-, 4-fluoro-2,3,6-trichloro-5-bromo-, 4-fluoro-2,3-dichloro-5,6-dibromo-, 4-fluoro-2,6-dichloro-3,5-dibromo-, 4-fluoro-3,5-dichloro-2,6-dibromo-, 4-fluoro-2,5-dichloro-3,6-dibromo-, 4-fluoro-2-chloro-3,5,6-tribromo- and 4-fluoro-3-chloro-2,5,6-tribromophenyl.

All of the above-described phenyl radicals $A^1$ can be combined together to form the inventive compounds IIIa, i.e. the inventive diphenyliodonium salts IIIa. It is, though, advantageous in accordance with the invention when the inventive diphenyliodonium salts III are symmetrical, i.e. that the two phenyl radicals $A^1$ have the same structure.

An example of such a combination, i.e. an inventive diphenyliodonium salt IIIa, is
3,3'-dibromo-4,4'-difluorodiphenyliodonium chloride.

In the general formula IIIb, the variable Y and the index q are each as defined above.

The variable $A^3$ represents a monovalent difluorinated phenyl radical or a monovalent, chlorinated, brominated and/or iodinated, difluorinated phenyl radical.

The phenyl radical $A^3$ preferably has the general formula XXIV:

(XXIV)

where the index n and the variable X are each as defined above.

Examples of suitable monovalent, difluorinated phenyl radicals $A^3$ are
2,3-, 2,4-, 2,5-, 2,6-, 3,4- and 3,5-difluorophenyl.

Examples of suitable monovalent, chlorinated, brominated and/or iodinated, difluorinated phenyl radicals $A^3$ are 2,3-, 2,4-, 2,5-, 2,6-, 3,4- and 3,5-difluorophenyl radicals which are substituted by at least one chlorine atom, at least one bromine atom and/or at least one iodine atom, preferably at least one chlorine atom and/or at least one bromine atom and in particular at least one chlorine atom. Examples of suitable chlorinated, difluorinated phenyl radicals $A^3$ are
2-, 4- and 6-chloro-3,5-difluorophenyl,
2,4- and 2,6-dichloro-3,5-difluorophenyl and
2,4,6-trichloro-3,5-difluorophenyl,
especially 2- and 4-chloro-3,5-difluorophenyl.

All of the above-described phenyl radicals $A^3$ can be combined with one another to give the inventive compounds IIIb, i.e. the inventive diphenyliodonium salts IIIb. It is, though, advantageous in accordance with the invention when the inventive diphenyliodonium salts IIIb are symmetrical, i.e. that the two phenyl radicals $A^3$ have the same structure.

One example of such a combination, i.e. an inventive diphenyliodonium salt IIIb, is
4,4'-dichloro-3,3',5,5'-tetrafluorodiphenyliodonium chloride.

1.5 The Inventive Compounds IV

The inventive compounds IV have the general formula IV:

$$A^1\text{-}(L)_p\text{-}A^1 \qquad (IV).$$

In the general formula IV, the index and the variables are each as defined above, at least one phenyl radical $A^1$ being chlorinated, brominated and/or iodinated.

The phenyl radicals $A^1$ may be combined in any manner to give the inventive compounds IV. In particular, the inventive compounds IV are biphenyls IV, diphenyl ethers IV and diphenylmethanes IV. The inventive biphenyls IV and diphenyl ethers IV preferably have no other substituents. The inventive diphenylmethanes IV preferably have at least one, in particular one, methyl group as other substituents.

Particularly advantageous inventive compounds IV are
2',3,3',4,5,5',6,6'-octabromo-2,4'-difluorodiphenyl ether and
4-methyl-2,2',5,6-tetrachloro-3,3'-difluoro-diphenylmethane.

1.6 The Inventive Compounds V

The inventive compounds V have the general formula V:

$$A^3\text{-}(L)_p\text{-}B^1 \qquad (V).$$

In the general formula V, the variables and the index are each as defined above, the monovalent phenyl radical $A^3$ being chlorinated, brominated and/or iodinated when the monovalent phenyl radical $B^1$ is not halogenated.

The phenyl radicals $A^3$ and $B^1$ may be combined in any manner to give the inventive compounds V. In particular, the inventive compounds V are biphenyls V, diphenyl ethers V and diphenylmethanes V. The inventive biphenyls V and diphenyl ethers V preferably have no other substituents. The inventive diphenylmethanes V preferably have at least one, in particular one, methyl group as other substituents.

Examples of particularly advantageous inventive compounds V are
2',4',4-trichloro-3,5-difluorobiphenyl and
4-methyl-2,2',5,6-tetrachloro-3,3'-difluoro-diphenylmethane.

1.7 The Inventive Compounds VI

The inventive compounds VI have the general formula VI:

(VI)

In the general formula VI, the variables and the index are each as defined above, at least one phenyl radical $A^2$ being chlorinated, brominated and/or iodinated.

The phenyl radicals $A^2$ may be combined in any manner to give the inventive compounds VI. In particular, the inventive compounds VI are dibenzofurans VI and dibenzo-p-dioxins VI. The inventive dibenzofurans VI and dibenzo-p-dioxins VI preferably have no other substituents.

Examples of particularly advantageous inventive compounds VI are
1,2,3,7,8,9-hexachloro-4,6-difluorodibenzofuran and
1,2,3,7,8,9-hexachloro-4,6-difluorodibenzo-p-dioxin.

1.8 The Inventive Compounds VII

The inventive compounds VII have the general formula VII:

(VII)

In the general formula VII, the variables L and $B^2$ and the index p are each as defined above, the divalent phenyl radical $A^4$ being chlorinated, brominated and/or iodinated when the divalent phenyl radical $B^2$ is not halogenated.

In the general formula IV, the variable $A^4$ is a divalent, difluorinated phenyl radical or a divalent chlorinated, brominated and/or iodinated, difluorinated phenyl radical. The divalent phenyl radical $A^4$ has the general formula XXV:

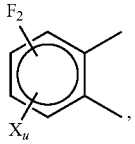

(XXV)

where the variable X is as defined above, in particular a chlorine atom and/or bromine atom, and the index u=0, 1 or 2.

Examples of suitable divalent difluorinated phenyl radicals $A^4$ are
3,4-, 3,5-, 3,6- and 4,5-difluorophen-1,2-ylene radicals.

Examples of suitable divalent, chlorinated, brominated and/or iodinated, difluorinated phenyl radicals $A^4$ are 3,4-, 3,5-, 3,6- and 4,5-difluorophen-1,2-ylene radicals which are substituted by at least one chlorine atom, at least one bromine atom and/or at least one iodine atom, preferably at least one chlorine atom and/or at least one bromine atom and in particular at least one chlorine atom. Examples of very suitable chlorinated, difluorinated phenyl radicals $A^4$ are
4-chloro- and 2-chloro-3,5-difluorophen-1,2-ylene and 2,4-dichloro-3,5-difluorophen-1,2-ylene.

The phenyl radicals $A^4$ and $B^2$ may be combined in any manner to give the inventive compounds VII. In particular, the inventive compounds are dibenzofurans and dibenzo-p-dioxins VII. The inventive dibenzofurans and dibenzo-p-dioxins VII preferably have no other substituents.

2. The Inventive Processes 1 to 3
2.1 Preliminary Remark

The inventive compounds I to VII may be prepared with the aid of customary and known low molecular weight organic chemistry processes. According to the invention, it is advantageous to prepare the inventive compounds I, IV and V with the aid of the inventive process 1, to prepare the inventive compounds I, II and IV to VII with the aid of the inventive process 2 and to prepare the inventive compounds III with the aid of the inventive process 3.

2.2 The Inventive Process 1

Inventive compounds I, IV and V, especially inventive diphenyl ethers I, IV and V, are prepared preferably with the aid of the inventive process 1.

In a first variant of the inventive process 1, a symmetrical difluorinated or tetrafluorinated iodonium salt of the general formula VIII:

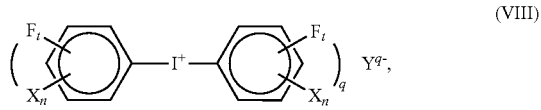

(VIII)

where the index and the variables are each defined as follows:
t is 1 or 2,
n is 0 or an integer from 1 to 4, where n=max. 3 when t=2,
q is an integer from 1 to 4, in particular 1 or 2,
X is chlorine, bromine and/or iodine, in particular chlorine and/or bromine, and
Y is an acid anion, in particular chloride or sulfate;
is reacted with a chlorinated, brominated and/or iodinated phenol, especially a chlorinated and/or brominated phenol, of the general formula IX

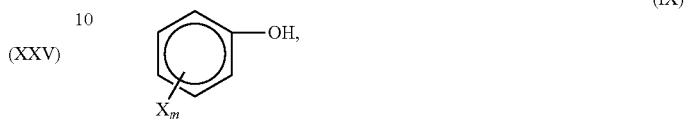

(IX)

where the index m=0 or an integer from 1 to 5 and the variable X is as defined above.

In this case, the index m is obligatorily an integer from 1 to 5 when the index n is 0.

Examples of suitable symmetrical difluorinated diphenyliodonium salts of the general formula VIII are the above-described inventive diphenyliodonium salts of the general formula III, and also 2,2'-, 3,3'- and 4,4'-difluorodiphenyliodonium salts.

Examples of suitable symmetrical tetrafluorinated diphenyliodonium salts of the general formula VIII are 3,3',4,4'-tetrafluorodiphenyliodonium chloride and 3,3',5,5'-tetrafluorodiphenyliodonium chloride.

Examples of suitable chlorinated, brominated and/or iodinated, especially chlorinated and/or brominated, phenols of the general formula IX are phenols which have one of the above-described phenyl radicals $B^1$ of the general formula XXI.

In the second variant of the inventive process 1, a symmetrical unfluorinated diphenyliodonium salt of the general formula X:

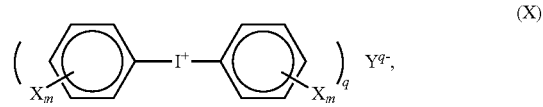

(X)

where the variables X and Y and the indices m and q are each as defined above;
is reacted with a monofluorinated or difluorinated phenol of the general formula XI:

(XI)

where the indices t and n, where n=max. 3 when t=2, and the variable X are each as defined above.

In this case, the index m is obligatorily an integer from 1 to 5 when the index n=0. Or else, the index n is obligatorily an integer from 1 to 4 or from 1 to 3 when the index m is 0.

Examples of suitable diphenyliodonium salts of the general formula X, such as 4,4'-dichloro-, 4,4'-dibromo- and 4,4'-diiododiphenyliodonium salts and polybrominated diphenyliodonium salts are described in the article by F. Marshall Beringer, Robert A. Falk, Marilyn Karniol, Irving Lillien, Giulio Masullo, Marvin Mausner and Erwin Sommer, "Diaryliodonium Salts. IX. The Synthesis of Substituted Diphenyl Iodonium Salts", Journal of the American Chemical Society, volume 81, pages 342 to 351, 1959, or in the article by Göran Marsh, Jiwei Hu, Eva Jokobsson, Sara Rahm, and Ake Bergman, "Synthesis and Characterization of 32 Polybrominated Diphenyl Ethers", Environmental Science and Technology, volume 33, pages 3033 to 3037, 1999.

The phenol of the general formula XI preferably contains a phenyl radical $A^1$ of the general formula XX.

Preference is given to using the first variant of the inventive process 1. Very particular preference is given to using the inventive diphenyliodonium salts III of the general formula III. In particular, 3,3'-dibromo-4,4'-difluorodiphenyliodonium chloride is used.

The inventive process is preferably carried out in the presence of a strong organic or inorganic base, especially of an inorganic base. Particular preference is given to using NaOH.

2.3 The Inventive Process 2

Inventive compounds I, II and IV to VII are preferably prepared with the aid of the inventive process 2.

2.3.1 Inventive Process 2—First Variant

In the first variant of the inventive process 2, a chlorinated, brominated and/or iodinated, aromatic compound having two benzene rings of its base structure of the general formula XII or XIII:

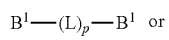
(XII)

(XIII)

is monofluorinated or difluorinated. This can be done by direct fluorination with elemental fluorine or with fluorinating agents such as xenon difluoride. However, it is also possible to employ the Schiemann reaction, in which the fluorination is effected by the decomposition of the corresponding diazonium tetrafluoroborate salts.

In the general formula XII or XIII, the variables $B^1$, $B^2$ and L and the index p are each as defined above, with the proviso that at least one of the phenyl radicals $B^1$ or $B^2$ is chlorinated, brominated and/or iodinated.

Examples of suitable aromatic compounds XII are halogenated biphenyls XII, diphenyl ethers XII and diphenylmethanes XII. Examples of suitable aromatic compounds XIII are dibenzo-p-dioxins XIII and dibenzofurans XIII. These compounds XII and XIII are known per se and are described in Römpp Online 2003, "Polychlorierte Biphenyle" [Polychlorinated Biphenyls], "PCB-Abbau" [PCB Degradation], "Polybromierte Biphenyle" [Polybrominated Biphenyls], "Schadstoff-Höchstmengen-Verordnung" [German Maximum Harmful Substance Levels Act], "Flammschutzmittel" [Flame Retardants] and "Dioxine" [Dioxins];

Mitchell D. Erickson, "Introduction: PCB Properties, Uses, Occurrence, and Regulatory History", in Roberston and Hanson (Editors), PCB, The University Press of Kentucky, pages xi to xxviii, 2001;

George M. Frame, "The Current State-of-the-Art of Comprehensive, Quantitative, Congener-Specific PCB Analysis, and What We Now Know about the Distributions of Individual Congeners in Commolercial Aroclor Mixtures", in Robertson and Hanson (Editors), PCB, The University Press of Kentucky, pages 3 to 9, 2001;

Hans-Joachim Lehmler, Carolyn P. Brock, Brian Patrick, Larry D. Robertson, "Synthesis of Polychlorinated Biphenyls (PCBs) and Their Metabolites Using the Suzuki-Coupling", in Robertson and Hanson (Editors), PCB, The University Press of Kentucky, pages 57 to 60, 2001;

Göran Marsh, Jiwei Hu, Eva Jokobsson, Sara Rahm, and Ake Bergman, "Synthesis and Characterization of 32 Polybrominated Diphenyl Ethers", Environmental Science and Technology, volume 33, pages 3033 to 3037, 1999;

Anders Garå, Kurt Andersson, Carl-Axel Nilsson and Ake Norström, "Synthesis of halogenated diphenyl ethers and dibenzofurans—A discussion of specific isomers available", Chemosphere; and Michael Herrmann, Umweltbundesamt, Postfach 33 00 22, 14191 Berlin, Federal Republic of Germany, "UGILEC" August 2002).

Examples of suitable compounds XIII are
1,2,3,7,8,9-hexachlorodibenzofuran,
1,2,3,7,8,9-hexachlorodibenzo-p-dioxin and
4-methyl-2,2',5,6-tetrachlorodiphenylmethane.

2.3.2 Inventive Process 2—Second Variant

In the second variant of the inventive process 2, a monofluorinated or difluorinated, aromatic compound having two benzene rings in its base structure of the general formula XIV to XIX:

(XIV)

(XV)

(XVI)

(XVII)

(XVIII)

(XIX)

where the indices and the variables are each as defined above, with the proviso that the phenyl radicals $A^1$ to $A^4$ and $B^1$ and $B^2$ are not chlorinated, brominated and/or iodinated; is chlorinated, brominated and/or iodinated in a manner known per se, especially chlorinated and/or brominated.

Examples of suitable compounds XIV to XIX are
4-fluorobiphenyl (XIV),
2,4'-difluorodiphenyl ether (XV),
3,5-difluorodiphenylmethane (XVI),
3-fluorodibenzofuran (XVII),
3,7-difluorodibenzo-p-dioxin (XVIII) and
1,3-difluorodibenzofuran (XIX),
in particular 2,4'-difluorodiphenyl ether (XV).

2.2.3 Inventive Process 2—Third Variant

The third variant of the inventive process 2 is preferably used for the preparation of inventive compounds I, IV or V, especially of biphenyls I, IV or V and diphenylmethanes I, IV or V.

In this variant, a chlorinated, brominated and/or iodinated benzene derivative is reacted with a brominated and/or iodinated, monofluorinated or difluorinated benzene or alkylbenzene, or a brominated and/or iodinated, chlorinated, monofluorinated or difluorinated benzene or alkylbenzene.

Examples of suitable benzene derivatives for the third variant of the inventive process 2 are chlorinated, brominated and/or iodinated benzeneboric acids which, under the conditions of the Suzuki coupling, can be reacted with the brominated and/or iodinated, monofluorinated or difluorinated benzenes or the brominated and/or iodinated, chlorinated, monofluorinated or difluorinated benzenes (cf. Hans-Joachim Lehmler, Carolyn P. Brock, Brian Patrick, Larry D. Robertson, "Synthesis of Polychlorinated Biphenyls (PCBs) and Their Metabolites Using the Suzuki-Coupling", in Robertson and Hanson (Editors), PCB, The University Press of Kentucky, pages 57 to 60, 2001).

The chlorinated, brominated and/or iodinated benzeneboric acid is preferably selected from the group consisting of
2-, 3- and 4-halobenzeneboric acid;
2,3-, 2,4-, 2,5-, 2,6-, 3,4- and 3,5-dihalobenzeneboric acid;
2,3,4-, 2,4,5-, 2,4,6- and 3,4,5-trihalobenzeneboric acid;
2,3,4,6- and 2,3,4,5-tetrahalobenzeneboric acid; and
pentahalobenzeneboric acid;
where the halogen is selected from the group consisting of chlorine, bromine and iodine.

The halogen is preferably selected from the group consisting of chlorine and bromine.

The chlorinated and/or brominated benzeneboric acid is more preferably selected from the group consisting of
2-, 3- and 4-chlorobenzeneboric acid;
2-, 3- and 4-bromobenzeneboric acid;
2-chloro-6-bromo-, 3-chloro-2-bromo-, 2-chloro-3-bromo-, 2-chloro-5-bromo-, 3-chloro-6-bromo-, 4-chloro-2-bromo- and 2-chloro-4-bromobenzeneboric acid;
2,4-dichloro-6-bromo-, 2,6-dichloro-4-bromo-, 4-chloro-2,6-dibromo-, 2-chloro-4,6-dibromo-, 2,3-dichloro-4-bromo-, 2,4-dichloro-3-bromo-, 3,4-dichloro-2-bromo-, 4-chloro-2,3-dibromo-, 3-chloro-2,4-dibromo-, 2-chloro-3,4-dibromo-, 3,4-dichloro-5-bromo-, 3,5-dichloro-4-bromo-, 3-chloro-4,5-dibromo- and 4-chloro-3,5-dibromobenzeneboric acid;
2,4,5-trichloro-6-bromo-, 2,4,6-trichloro-3-bromo-, 2,3,6-trichloro-4-bromo-, 2,3,4-trichloro-5-bromo- and 2,3,4-trichloro-6-bromo-, 2,4-dichloro-5,6-dibromo-, 2,5-dichloro-4,6-dibromo-, 3,4-dichloro-2,6-dibromo-, 2,6-dichloro-3,4-dibromo-, 2,4-dichloro-3,6-dibromo-, 2-chloro-4,5,6-tribromo-, 3-chloro-4,5,6-tribromo-, 4-chloro-2,5,6-tribromo-, 4-chloro-3,5,6-tribromo-, 3-chloro-2,4,6-tribromo- and 2-chloro-3,4,6-tribromobenzeneboric acid;
2,3,4,5-tetrachloro-6-bromo-, 2,3,4,6-tetrachloro-5-bromo-, 2,3,5,6-tetrachloro-4-bromo-, 2,2,4-trichloro-5,6-dibromo-, 2,4,5-trichloro-3,6-dibromo-, 3,4,5-trichloro-2,6-dibromo-, 2,3-dichloro-4,5,6-tribromo-, 2,4-dichloro-3,5,6-tribromo-, 2,5-dichloro-3,4,6-tribromo-, 2,6-dichloro-3,4,5-tribromo-, 2-chloro-3,4,5,6-tetrabromo-, 3-chloro-2,4,5,6-tetrabromo- and 4-chloro-2,3,5,6-tetrabromobenzeneboric acid; and
pentachloro- and pentabromobenzeneboric acid.

Examples of suitable alkylbenzenes as base structures of the monofluorinated or difluorinated alkylbenzenes are toluene, xylene and cresol.

Preferably,
the brominated and/or iodinated, monofluorinated or difluorinated benzene is selected from the group consisting of 1,2-, 1,4- and 1,3-dihalo-, 1,2,3-, 1,2,4- and 1,3,5-trihalo-, 1,2,3,4-, 1,2,3,5- and 1,2,4,5-tetrahalo-, pentahalo- and hexahalobenzene in which one or two fluorine and at least one halogen selected from the group consisting of bromine and iodine are present.

Preferably,
the brominated and/or iodinated, chlorinated, monofluorinated or difluorinated benzene is selected from the group consisting of 1,2,3-, 1,2,4- and 1,3,5-trihalo-, 1,2,3,4-, 1,2,3,5- and 1,2,4,5-tetrahalo-, pentahalo- and hexahalobenzene in which one or two fluorine, at least one chlorine and at least one halogen selected from the group consisting of bromine and iodine are present.

The halogen is preferably selected from the group consisting of chlorine and bromine.

An example of a suitable chlorinated and brominated, difluorinated benzene is 1,3-difluoro-2-chloro-5-bromobenzene.

The brominated and/or iodinated, monofluorinated alkylbenzene which may optionally also be chlorinated is preferably selected from the group consisting of
2-fluoro- and 3-fluoro-4-bromomethyltoluene and 2-fluoro- and 3-fluoro-4-iodomethyltoluene.

Generally, in the third variant of the inventive process 2, the selection of the reactants is made such that
the resulting inventive biphenyls I and diphenylmethanes I contain the above-described phenyl radicals $A^1$ of the general formula XX and the above-described phenyl radicals $B^1$ of the general formula XXI,
the resulting inventive biphenyls IV and diphenylmethanes IV contain the above-described phenyl radicals $A^1$ of the general formula XX or
the resulting inventive biphenyls V and diphenylmethanes V contain the above-described phenyl radicals $A^3$ and the above-described phenyl radicals $B^1$ of the general formula XXI.

The person skilled in the art can therefore make the selection of the suitable reactants in a simple manner with reference firstly to the target compounds and secondly to the reactive functional groups required for the particular coupling reactions.

However, it is also possible to employ other coupling reactions such as Negishi coupling, the "Stille reaction" or the Kumada coupling. Preference is given to using Suzuki coupling.

2.3.4 Inventive Process 2—Fourth Variant

The fourth variant of the inventive process 2 is also preferably used for the preparation of inventive compounds I, IV and V. In this variant, a chlorinated, brominated and/or iodinated, monofluorinated or difluorinated benzene derivative is reacted with a brominated and/or iodinated benzene or alkylbenzene or a brominated and/or iodinated, chlorinated benzene or alkylbenzene.

Examples of suitable monofluorinated or difluorinated benzene derivatives for the fourth variant of the inventive process 2 are optionally chlorinated, brominated and/or iodinated, monofluorinated or difluorinated benzeneboric acids which, under the conditions of the Suzuki coupling, can be reacted with the brominated and/or iodinated benzenes or alkylbenzenes or the brominated and/or iodinated, chlorinated benzenes or alkylbenzenes.

The chlorinated, brominated and/or iodinated, monofluorinated benzene derivative is preferably a monofluorinated benzeneboric acid or a chlorinated, brominated and/or iodinated, monofluorinated benzeneboric acid.

The monofluorinated benzeneboric acid is preferably selected from the group consisting of
2-, 3- and 4-fluorobenzeneboric acid.
The chlorinated, brominated and/or iodinated, monofluorinated benzeneboric acid is preferably selected from the group consisting of
2-fluoro-3-halo-, 2-fluoro-4-halo-, 2-fluoro-5-halo- and 2-fluoro-6-halobenzeneboric acid;
3-fluoro-2-halo-, 3-fluoro-4-halo-, 3-fluoro-5-halo- and 3-fluoro-6-halobenzeneboric acid;
4-fluoro-2-halo- and 4-fluoro-3-halobenzeneboric acid;
2-fluoro-3,4-dihalo-, 2-fluoro-3,5-dihalo-, 2-fluoro-3,6-dihalo-, 2-fluoro-4,5-dihalo- and 2-fluoro-4,6-dihalobenzeneboric acid;
3-fluoro-2,4-dihalo-, 3-fluoro-2,5-dihalo-, 3-fluoro-2,6-dihalo-, 3-fluoro-4,5-dihalo-, 3-fluoro-4,6-dihalo- and 3-fluoro-5,6-dihalobenzeneboric acid;
4-fluoro-2,3-dihalo-, 4-fluoro-2,5-dihalo-, 4-fluoro-3,5-dihalo- and 4-fluoro-2,6-dihalobenzeneboric acid;
2-fluoro-3,4,5-trihalo-, 2-fluoro-3,4,6-trihalo- and 2-fluoro-4,5,6-trihalobenzeneboric acid;
3-fluoro-2,4,5-trihalo-, 3-fluoro-2,4,6-trihalo- and 3-fluoro-4,5,6-trihalobenzeneboric acid;
4-fluoro-2,3,5-trihalo- and 4-fluoro-2,5,6-trihalobenzeneboric acid; and
2-fluoro-3,4,5,6-tetrahalo-, 3-fluoro-2,4,5,6-tetrahalo- and 4-fluoro-2,3,5,6-tetrahalobenzeneboric acid;
where the halogen is selected from the group consisting of chlorine, bromine and iodine.

The halogen is more preferably selected from the group consisting of chlorine and bromine.

The chlorinated and/or brominated, monofluorinated benzeneboric acid is most preferably selected from the group consisting of
2-fluoro-3-chloro-, 2-fluoro-4-chloro-, 2-fluoro-5-chloro- and 2-fluoro-6-chlorobenzeneboric acid;
3-fluoro-2-chloro-, 3-fluoro-4-chloro-, 3-fluoro-5-chloro- and 3-fluoro-6-chlorobenzeneboric acid;
4-fluoro-2-chloro- and 4-fluoro-3-chlorobenzeneboric acid;
2-fluoro-3-bromo-, 2-fluoro-4-bromo-, 2-fluoro-5-bromo- and 2-fluoro-6-bromobenzeneboric acid;
3-fluoro-2-bromo-, 3-fluoro-4-bromo-, 3-fluoro-5-bromo- and 3-fluoro-6-bromobenzeneboric acid;
4-fluoro-2-bromo- and 4-fluoro-3-bromobenzeneboric acid;
2-fluoro-4-chloro-3-bromo-, 2-fluoro-3-chloro-4-bromo-, 2-fluoro-5-chloro-3-bromo-, 2-fluoro-3-chloro-5-bromo-, 2-fluoro-6-chloro-3-bromo-, 2-fluoro-3-chloro-6-bromo-, 2-fluoro-5-chloro-4-bromo-, 2-fluoro-4-chloro-5-bromo-, 2-fluoro-6-chloro-4-bromo-, 2-fluoro-4-chloro-6-bromo-, 2-fluoro-5-chloro-6-bromo- and 2-fluoro-6-chloro-5-bromobenzeneboric acid;
3-fluoro-4-chloro-2-bromo-, 3-fluoro-2-chloro-4-bromo-, 3-fluoro-5-chloro-2-bromo-, 3-fluoro-2-chloro-5-bromo-, 3-fluoro-6-chloro-2-bromo-, 3-fluoro-2-chloro-6-bromo-, 3-fluoro-5-chloro-4-bromo-, 3-fluoro-4-chloro-5-bromo-, 2-fluoro-6-chloro-4-bromo-, 3-fluoro-4-chloro-6-bromo-, 3-fluoro-6-chloro-5-bromo- and 3-fluoro-5-chloro-6-bromobenzeneboric acid;
4-fluoro-3-chloro-2-bromo-, 4-fluoro-2-chloro-3-bromo-, 4-fluoro-2-chloro-5-bromo-, 4-fluoro-5-chloro-3-bromo- and 4-fluoro-2-chloro-6-bromobenzeneboric acid;
2-fluoro-4,5-dichloro-3-bromo-, 2-fluoro-3,5-dichloro-4-bromo-, 2-fluoro-3,4-dichloro-5-bromo, 2-fluoro-5-chloro-3,4-dibromo-, 2-fluoro-4-chloro-3,5-dibromo-, 2-fluoro-3-chloro-4,5-dibromo-, 2-fluoro-3,4-dichloro-3-bromo-, 2-fluoro-3,6-dichloro-4-bromo-, 2-fluoro-3,4-dichloro-6-bromo-, 2-fluoro-6-chloro-3,4-dibromo-, 2-fluoro-4-chloro-3,6-dibromo-, 2-fluoro-3-chloro-4,6-dibromo-, 2-fluoro-5,6-dichloro-4-bromo-, 2-fluoro-4,6-dichloro-5-bromo-, 2-fluoro-4,5-dichloro-6-bromo-, 2-fluoro-6-chloro-4,5-dibromo-, 2-fluoro-5-chloro-4,6-dibromo- and 2-fluoro-4-chloro-5,6-dibromobenzeneboric acid;
3-fluoro-4,5-dichloro-2-bromo-, 3-fluoro-2,5-dichloro-4-bromo-, 3-fluoro-2,4-dichloro-5-bromo-, 3-fluoro-4-chloro-2,5-dibromo-, 3-fluoro-2-chloro-4,5-dibromo-, 3-fluoro-5-chloro-2,4-dibromo-, 3-fluoro-4,6-dichloro-2-bromo-, 3-fluoro-2,6-dichloro-4-bromo-, 3-fluoro-6-chloro-2,4-dibromo-, 3-fluoro-4-chloro-2,6-dibromo-, 3-fluoro-2-chloro-4,6-dibromo-, 3-fluoro-5,6-dichloro-4-bromo-, 3-fluoro-4,6-dichloro-5-bromo-, 3-fluoro-4,5-dichloro-6-bromo-, 3-fluoro-6-chloro-4,5-dibromo-, 3-fluoro-4-chloro-5,6-dibromo- and 3-fluoro-5-chloro-4,6-dibromobenzeneboric acid;
4-fluoro-2,3-dichloro-5-bromo-, 4-fluoro-2,5-dichloro-3-bromo-, 4-fluoro-3,5-dichloro-2-bromo-, 4-fluoro-3-chloro-5,6-dibromo-, 4-fluoro-3-chloro-2,5-dibromo-, 4-fluoro-2-chloro-3,5-dibromo-, 4-fluoro-2,3-dichloro-6-bromo-, 4-fluoro-2,6-dichloro-3-bromo-, 4-fluoro-2,5-dichloro-6-bromo-, 4-fluoro-2-chloro-5,6-dibromo-, 4-fluoro-2-chloro-3,6-dibromo- and 4-fluoro-3-chloro-2,6-dibromobenzeneboric acid;
2-fluoro-4,5,6-trichloro-3-bromo-, 2-fluoro-3,5,6-trichloro-4-bromo-, 2-fluoro-3,4,6-trichloro-5-bromo-, 2-fluoro-3,4,5-trichloro-6-bromo-, 2-fluoro-5,6-dichloro-3,4-dibromo-, 2-fluoro-4,6-dichloro-3,5-dibromo-, 2-fluoro-4,5-dichloro-3,6-dibromo-, 2-fluoro-3,6-dichloro-4,5-dibromo-, 2-fluoro-3,5-dichloro-4,6-dibromo-, 2-fluoro-3,4-dichloro-5,6-dibromo-, 2-fluoro-3-chloro-4,5,6-tribromo-, 2-fluoro-4-chloro-3,5,6-tribromo-, 2-fluoro-5-chloro-3,4,6-tribromo- and 2-fluoro-6-chloro-3,4,5-tribromobenzeneboric acid;
3-fluoro-4,5,6-trichloro-2-bromo-, 3-fluoro-2,5,6-trichloro-4-bromo-, 3-fluoro-2,4,6-trichloro-5-bromo-, 3-fluoro-2,4,5-trichloro-6-bromo-, 3-fluoro-5,6-dichloro-2,4-dibromo-, 3-fluoro-4,6-dichloro-2,5-dibromo-, 3-fluoro-4,5-dichloro-2,6-dibromo-, 3-fluoro-2,4-dichloro-5,6-dibromo-, 3-fluoro-2,5-dichloro-4,6-dibromo-, 3-fluoro-2,6-dichloro-4,5-dibromo-, 3-fluoro-6-chloro-2,4,5-tribromo-, 3-fluoro-5-chloro-2,4,6-tribromo-, 3-fluoro-4-chloro-2,5,6-tribromo- and 3-fluoro-2-chloro-4,5,6-tribromobenzeneboric acid; and
4-fluoro-2,3,5-trichloro-6-bromo-, 4-fluoro-2,3,6-trichloro-5-bromo-, 4-fluoro-2,3-dichloro-5,6-dibromo-, 4-fluoro-2,6-dichloro-3,5-dibromo-, 4-fluoro-3,5-dichloro-2,6-dibromo-, 4-fluoro-2,5-dichloro-3,6-dibromo-, 4-fluoro-2-chloro-3,5,6-tribromo- and 4-fluoro-3-chloro-2,5,6-tribromobenzeneboric acid.

Preference is given to selecting
the brominated and/or iodinated benzene from the group consisting of monohalo-, 1,2-, 1,4- and 1,3-dihalo-, 1,2,3-, 1,2,4- and 1,3,5-trihalo-, 1,2,3,4-, 1,2,3,5- and 1,2,4,5-tetrahalo-, pentahalo- and hexahalobenzene, where the halogen is selected from the group consisting of bromine and iodine; and
the brominated and/or iodinated, chlorinated benzene from the group consisting of 1,3-dihalo-, 1,2,3-, 1,2,4- and 1,3,5-trihalo-, 1,2,3,4-, 1,2,3,5- and 1,2,4,5-tetrahalo-, pentahalo- and hexahalobenzene, where at least one chlorine and at least one halogen selected from the group consisting of bromine and iodine is present.

Preference is given to selecting the brominated and/or iodinated, chlorinated alkylbenzene from the group consisting of 2-chloro-, 3-chloro-, 2,6-dichloro-, 2,5-dichloro-, 3,5-dichloro-, 2,3,5-trichloro-, 2,3,6-trichloro-4-bromoethyltoluene and -4-iodomethyltoluene.

Generally, in the fourth variant of the inventive process 2, the selection of the reactants is made such that the resulting inventive biphenyls I and diphenylmethanes I contain the above-described phenyl radicals $A^1$ of the general formula XX and the above-described phenyl radicals $B^1$ of the general formula XXI and the resulting inventive biphenyls IV and diphenylmethanes IV contain the above-described phenyl radicals $A^1$ of the general formula XX or the resulting inventive biphenyls V and diphenylmethanes V contain the above-described phenyl radicals $A^3$ and the above-described phenyl radicals $B^1$ of the general formula XXI.

The person skilled in the art can therefore make the selection of the suitable reactants in a simple manner firstly on the basis of the target compounds and secondly on the basis of the reactive functional groups required for the particular coupling reactions.

However, it is also possible to use other coupling reactions such as Negishi coupling, the "Stille reaction" or Kumada coupling. Preference is given to using Suzuki coupling.

2.4 The Inventive Process 3

Preference is given to preparing the inventive compounds III with the aid of the inventive process 3.

In the inventive process 3, a chlorinated, brominated and/or iodinated, especially chlorinated and/or brominated, monofluorinated or difluorinated benzene is reacted with iodyl sulfate.

Suitable chlorinated, brominated and/or iodinated, especially chlorinated and/or brominated, monofluorinated benzenes are those which afford the above-described phenyl radicals $A^1$ of the general formula XX. Of course, this can only be the case when the chlorinated, brominated and/or iodinated, especially chlorinated and/or brominated, monofluorinated benzenes still have at least one hydrogen atom. The person skilled in the art can therefore easily select the suitable chlorinated, brominated and/or iodinated, especially chlorinated and/or brominated, monofluorinated benzenes on the basis of the target compounds.

Suitable chlorinated, brominated and/or iodinated, especially chlorinated and/or brominated, difluorinated benzenes are those which afford the above-described phenyl radicals $A^1$ of the general formula XX. Of course, this can only be the case when the chlorinated, brominated and/or iodinated, especially chlorinated and/or brominated, monofluorinated benzenes still have at least one hydrogen atom. The person skilled in the art can therefore easily select the suitable chlorinated, brominated and/or iodinated, especially chlorinated and/or brominated, monofluorinated benzenes on the basis of the target compounds.

Suitable chlorinated, brominated and/or iodinated, especially chlorinated and/or brominated, difluorinated benzenes are those which afford the above-described phenyl radicals $A^3$. Of course, this can only be the case when the chlorinated, brominated and/or iodinated, especially chlorinated and/or brominated, difluorinated benzenes still have at least one hydrogen atom. The person skilled in the art can therefore easily select the suitable chlorinated, brominated and/or iodinated, especially chlorinated and/or brominated, difluorinated benzenes on the basis of the target compounds.

Preference is given to selecting the chlorinated, brominated and/or iodinated, monofluorinated or difluorinated benzene from the group consisting of 1,2-, 1,4- and 1,3-dihalo-, 1,2,3-, 1,2,4- and 1,3,5-trihalo-, 1,2,3,4-, 1,2,3,5- and 1,2,4,5-tetrahalo- and pentahalobenzene, where one or two fluorine and at least one halogen selected from the group consisting of chlorine, bromine and iodine are present.

In terms of method, the inventive process 3 has no special features, and can, for example, be carried out analogously to the processes described in the articles by F. Marshall Beringer, Robert A. Falk, Marilyn Karniol, Irving Lillien, Giulio Masullo, Marvin Mausner and Erwin Sommer "Diaryliodonium Salts. IX. The Synthesis of Substituted Diphenyl Iodonium Salts", in Journal of the American Chemical Society, volume 81, pages 342 to 351, 1959, or by Göran Marsh, Jiwei Hu, Eva Jokobsson, Sara Rahm, and Ake Bergman, "Synthesis and Characterization of 32 Polybrominated Diphenyl Ethers", in Environmental Science and Technology, volume 33, pages 3033 to 3037, 1999.

It is a very particular advantage of the inventive processes 1 to 3 that they make available an exceptionally large number of new mixed halogenated compounds, i.e. the inventive compounds I to VII. Among these, especially the inventive compounds I, II and IV to VII have the particular advantage that they can be used in an outstanding manner in the analysis of organic compounds, preferably halogenated organic compounds, particularly preferably halogenated aromatic compounds, especially chlorinated, brominated and/or iodinated diphenyl ethers, biphenyls, diphenylmethanes, dibenzo-p-dioxins and dibenzofurans, especially in environmental analysis, toxicology, biochemistry and medicine, especially as internal standards or surrogate standards which, together with their parent compounds, i.e. the unfluorinated, congeneric, chlorinated, brominated and/or iodinated diphenyl ethers, biphenyls, diphenylmethanes, dibenzo-p-dioxins and dibenzofurans, pass through physical, chemical and/or biological processes and are then detected and/or analyzed together with them or separately from them, as external standards which, in place of their parent compounds, pass through physical, chemical and/or biological processes for the purposes of calibrating these processes and are analyzed and/or detected separately from the parent compounds, and/or as model compounds which, in place of their parent compounds, pass through chemical and/or biological processes for the purposes of elucidating the reaction mechanisms and whose reaction products are detected and/or analyzed.

This allows the analysis of the unfluorinated parent compounds to be improved significantly.

EXAMPLES

Example 1

The Preparation of 3,3'-dibromo-4,4'-difluorodiphenyliodonium chloride

A mixture of concentrated sulfuric acid (1.9 ml) and 30 percent fuming sulfuric acid (3.75 ml) was added with stirring to iodine (1.59 g; 6.25 mmol). A mixture of concentrated sulfuric acid (0.5 ml), 30 percent fuming sulfuric acid (0.75 ml) and 100 percent fuming nitric acid (0.81 ml) was added slowly to the resulting mixture. The reaction mixture was stirred at from 70 to 80° C. over 1.5 hours, in the course of which yellow crystals of iodyl sulfate separate out. When the color of iodine had not yet disappeared fully, more fuming nitric acid was added dropwise. The resulting mixture was cooled to 0° C. and 2-bromofluorobenzene (5.47 g; 31.25 mmol; 3.42 ml) was slowly added dropwise. The resulting reaction mixture was stirred at 45° C. over two hours and then cooled to 0° C. 12.5 ml of water were added cautiously (exothermic reaction!). The nitrogen oxides formed were removed by passing a nitrogen stream through the reaction mixture. The aqueous phase was decanted off and the oily residue was taken up with methanol. The diphenyliodonium salt was precipitated by dropwise addition of concentrated hydrochloric acid. The crude yield was 4.01 g (7.86 mmol; 62.9%). The following analytical data were obtained:

Melting point: 160.3° C.;

$^1$H NMR (DMSO-$d_6$) δ 8.67 (H2', dd, J=2.1, 6.5 Hz), 8.26 (H6, H6', ddd, J=2.2, 4.6, 8.8 Hz), 7.52 (H5, H5', dd, J=8.8, 8.8 Hz);

$^{13}$C NMR (DMSO-$d_6$) δ 160 (C4, C4', d, J=250 Hz), 139 (C2, C2'), 137 (C6, C6', d, J=8 Hz), 120 (C5, C5', d, J=23 Hz), 110 (C3, C3', d, J=22 Hz), 158 and 116 not identifiable.

3,3'-Dibromo-4,4'-difluorodiphenyliodonium chloride was outstandingly suitable for the preparation of a wide variety of different halogenated monofluorinated diphenyl ethers.

Example 2

The Preparation of 4'-fluoro-2,3',4-tribromodiphenyl ether 2,4-Dibromophenol (0.63 g; 2.5 mmol) was dissolved in an aqueous solution (20 ml) of NaOH (0.1 g; 2.5 mmol). 3,3'-Dibromo-4,4'-difluorodiphenyliodonium chloride of Example 1 (1.58 g; 2.5 mmol) was added to the solution. The resulting reaction mixture was heated at reflux over 15 minutes, in the course of which the reaction mixture separated into a clear aqueous phase and an oily phase of higher density. After the reaction mixture had cooled, it was extracted with ether (2×30 ml). The combined extracts were washed with water and dried over sodium sulfate. The solution was filtered and the solvent was evaporated off. The crude product was purified on an open silica gel column with n-hexane as the mobile phase. The yield was 0.63 g (1.48 mmol; 59.3%). The following analytical data were obtained:

Colorless oil, purity >99%;

$^1$H NMR (CDCl$_3$) δ 7.79 (H3', d, J=2.3 Hz), 7.42 (H5', dd, J=2.3 and 8.7 Hz), 7.15 (H2, dd, J=3.0 and 5.5 Hz), 7.11 (H5, dd, J=7.9 and 9.0 Hz), 6.9 (H6, ddd, J=3.0, 3.9 and 9.0 Hz), 6.84 (H6', d, J=8.7 Hz);

$^{13}$C NMR (CDCl$_3$) δ 156 (C4, d, J=244 Hz), 153 (C1, d, J=3 Hz), 153 (C1'), 137 (C3'), 132 (C5'), 123 (C6'), 122 (C4'), 119 (C2, d, J=7 Hz), 118 (C2'), 117 (C5, d, J=24 Hz), 116 (C6), 110 (C5, d, J=23 Hz).

4'-Fluoro-2,3',4-tribromodiphenyl ether was usable in an outstanding manner in the analysis of brominated diphenyl ethers.

Example 3

The Preparation of 4'-fluoro-2,3',6-tribromodiphenyl ether 2,6-Dibromophenol (1.42 g; 5.6 mmol) was dissolved in an aqueous solution (45 ml) of NaOH (0.2 g; 5.6 mmol). 3,3'-Dibromo-4,4'-difluorodiphenyliodonium chloride of Example 1 (2.88 g; 5.6 mmol) was added to the solution. The resulting reaction mixture was heated at reflux over 1.5 hours, in the course of which the reaction mixture separated into a clear aqueous phase and an oily phase of higher density. After the reaction mixture had cooled, it was extracted with ether (2×50 ml). The combined extracts were washed with water and dried over sodium sulfate. The solution was filtered and the solvent was evaporated off. The crude product was purified on an open silica gel column with n-hexane as the mobile phase. The yield was 1.1 g (2.6 mmol; 46.1%). The following analytical data were obtained:

White crystals, purity >99%;

$^1$H NMR (CDCl$_3$) δ 7.63 (H3 and H5', d, J=8.1 Hz), 7.06 (H5 and H4' overlapping, dd, J=8.1, 8.1 and 8.7 Hz), 7.01 (H2, dd, J=3.0 and 5.5 Hz), 6.73 (H6, ddd, J=3.1, 3.4 and 9.0 Hz);

$^{13}$C NMR (CDCl$_3$) δ 155 (C4, d, J=242 Hz), 151 (C1), 149 (C1'), 133 (C3' and C5'), 128 (C4'), 120 and 119 (C2 or C2' and C6', inclusive), 117 (C5, d, J=24 Hz), 116 (C6, d, J=7 Hz), 110 (C3, d, J=23 Hz).

4'-Fluoro-2,3',6-tribromodiphenyl ether was usable in an outstanding manner in the analysis of brominated diphenyl ethers.

Example 4

The Preparation of 4'-fluoro-2,3',4,6-tetrabromodiphenyl ether 2,4,6-tribromophenol (1.92 g; 5.8 mmol) was dissolved in an aqueous solution (47 ml) of NaOH (0.24 g; 5.8 mmol). 3,3'-Dibromo-4,4'-difluorodiphenyliodonium chloride of Example 1 (2.96 g; 5.8 mmol) was added to the solution. The resulting reaction mixture was heated at reflux over 1.5 hours, in the course of which the reaction mixture separated into a clear aqueous phase and an oily phase of higher density. After the reaction mixture had cooled, it was extracted with ether (3×80 ml). The combined extracts were washed with water and dried over sodium sulfate. The solution was filtered and the solvent was evaporated off. The crude product was purified twice on an open silica gel column (once under nitrogen) with n-hexane as the mobile phase and recrystallized from methanol. The yield was 0.15 g (0.29 mmol; 4.9%). The following analytical data were obtained:

Pure white crystals, purity >98%;

$^1$H NMR (CDCl$_3$) δ 7.78 (H3' and H5', s), 7.06 (H5, dd, J=7.9 and 9.0 Hz), 7.0 (H2, dd, J=3.0 and 5.4 Hz), 6.73 (H6, ddd, J~3.1, 3.4 and 9.0 Hz);

$^{13}$C NMR (CDCl$_3$) δ 155 (C4, d, J=243 Hz), 152 (C1, d, J=3 Hz), 148 (C1'), 136 (C3' and C5'), 120 (C4'), 120 (C2), 119 (C2' and C6'), 117 (C5, d, J=24 Hz), 116 (C6, d, J=7 Hz), 110 (C3, d, J=23 Hz).

4'-Fluoro-2,3',4,6-tetrabromodiphenyl ether was usable in an outstanding manner in the analysis of brominated diphenyl ethers.

Example 5

The Preparation of 4'-fluoro-2,3,3',4,5,6-hexabromodiphenyl ether

Pentabromophenol (8.86 g; 18.1 mmol) was dissolved in an aqueous solution (145 ml) of NaOH (0.72 g; 18.1 mmol). 3,3'-Dibromo-4,4'-difluorodiphenyliodonium chloride of Example 1 (2.96 g; 5.8 mmol) was added to the solution. The resulting reaction mixture was heated at reflux over 1.5 hours, in the course of which the reaction mixture separated into a clear aqueous phase and an oily phase of higher density. After the reaction mixture had been cooled, it was extracted with ether (3×80 ml) and chloroform (2×50 ml). The combined ether extracts and the combined chloroform extracts were washed separately with water. The aqueous phases with which the combined ether extracts had been washed were washed with ether, and the aqueous phase with which the combined chloroform extracts had been washed was washed with chloroform. The combined organic phases were dried over sodium sulfate. The solution was filtered and the solvents were evaporated off. The crude product was purified on an open silica gel column under nitrogen with n-hexane as the mobile phase and recrystallized from methanol. The yield was 1.05 g (1.58 mmol; 8.7%). The following analytical data were obtained.

Pure white crystals; purity >99%;

$^1$H NMR (CDCl$_3$) δ 7.0 (H5, dd, J=7.9 and 9.0 Hz), 6.93 (H6, dd, J=3.1 and 5.5 Hz), 6.63 (H2, ddd, J~3.1, 3.6 and 9.0 Hz);

$^{13}$C NMR (CDCl$_3$) δ 155 (C4, d, J=243 Hz), 152 (C1, d, J=3 Hz), 150 (C1'), 136 (C3' and C5'), 129 (C3' and C5'), 127 (C4'), 122 (C2' and C6'), 120 (C2), 117 (C5, d, J=24 Hz), 115 (C6, d, J=7 Hz), 110 (C3, d, J=23 Hz).

4'-Fluoro-2,3,3',4,5,6-hexabromodiphenyl ether was usable in an outstanding manner in the analysis of brominated diphenyl ethers.

Example 6

The Preparation of 2,4,4'-trichloro-3'-fluorobiphenyl

Under an inert gas blanket, 5 ml of an aqueous, two molar sodium carbonate solution were added to a solution of 5 mmol of 1-fluoro-2-chloro-5-bromobenzene and 0.18 mg of Pd(PPh$_3$)$_4$ in ml of toluene. A solution of 5 mmol of 2,4-dichlorobenzeneboric acid in 10 ml of ethanol was added to the resulting mixture under an inert gas blanket. The reaction mixture was heated to 80° C. under inert gas over one hour. Thereafter, the reaction was ended by adding 0.5 ml of Perhydrol. Subsequently, the reaction mixture was stirred over another 4 hours, after which it was taken up with 20 ml of diethyl ether. The water-soluble constituents of the resulting mixture were removed by shaking with water. The removed organic phase was dried with magnesium sulfate. After the desiccant had been removed, the organic solution was concentrated by evaporation and the resulting crude product was purified by recrystallization. The recrystallized product was characterized by mass spectrometry (cf. Table 1).

2,4,4'-Trichloro-3'-fluorobiphenyl was usable in an outstanding manner in the analysis of chlorinated biphenyls.

TABLE 1

Mass spectrum of 2,4,4'-trichloro-3'-fluorobiphenyl

| m/z | Ion | Intensity (%) |
|---|---|---|
| 280 | M$^+$ (C$_{12}$H$_6$Cl$_3$F) | 31 |
| 278 | M$^+$ | 96 |
| 276 | M$^+$ | 100 |
| 274 | M$^+$ | 3 |
| 243 | M$^+$—Cl | 1 |
| 241 | M$^+$—Cl | 4 |
| 239/238 | M$^+$—Cl | 6 |
| 206 | M$^+$—Cl$_2$ | 14 |
| 204 | M$^+$—Cl$_2$ | 45 |
| 169/168 | M$^+$—Cl$_2$—Cl | 32 |
| 137 | M$^{++}$ | 7 |

Example 7

The Preparation of 4-methyl-2,2',5,6-tetrachloro-3'-fluorodiphenylmethane

4-Methyl-2,2',5,6-tetrachlorodiphenylmethane was fluorinated directly with Fluorselect® in an inert organic solvent. Subsequently, any Fluorselect® still present was reduced. The water-soluble constituents of the resulting mixture were removed by shaking with water. The organic phase was dried with magnesium sulfate. After the desiccant had been removed, the organic phase was concentrated by evaporation and the resulting crude product was purified by recrystallization and characterized by mass spectrometry (cf. Table 2).

4-Methyl-2,2',5,6-tetrachloro-3'-fluorodiphenylmethane was usable in an outstanding manner in the analysis of chlorinated diphenylmethanes (UGILEC®).

TABLE 2

Mass spectrum of 4-methyl-2,2',5,6-tetrachloro-3'-fluorodiphenylmethane

| m/z | Ion | Intensity (%) |
|---|---|---|
| 342 | M$^+$ | 10 |
| 340 | M$^+$ | 48 |
| 338 | M$^+$ | 100 |
| 336 | M$^+$ | 78 |
| 321 | M$^+$—CH$_3$ | 2 |
| 305 | M$^+$—Cl | 2 |
| 303 | M$^+$—Cl | 6 |
| 301 | M$^+$—Cl | 7 |
| 288 | M$^+$—Cl—CH$_3$ | 2 |
| 270 | M$^+$—Cl$_2$ | 4 |
| 268 | M$^+$—Cl$_2$ | 23 |
| 266 | M$^+$—Cl$_2$ | 36 |
| 251 | M$^+$—Cl$_2$—CH$_3$ | 4 |
| 233 | M$^+$—Cl$_2$—Cl | 1 |
| 231 | M$^+$—Cl$_2$—Cl | 4 |
| 216 | M$^+$—Cl$_2$—Cl—CH$_3$ | 2 |
| 209 | C$_8$H$_6$Cl$_3$ | 9 |
| 207 | C$_8$H$_6$Cl$_3$ | 7 |
| 196 | M$^+$—Cl$_2$—Cl$_2$ | 28 |
| 192 | C$_7$H$_4$Cl$_3$ | 8 |
| 190 | C$_7$H$_4$Cl$_3$ | 6 |
| 176 | M$^+$—Cl$_2$—Cl$_2$—HF | 2 |
| 181 | M$^+$—Cl$_2$—Cl$_2$—CH$_3$ | 2 |
| 169 | M$^{++}$ | 11 |
| 168 | M$^{++}$ | 9 |
| 145 | C$_7$H$_5$ClF | 6 |
| 143 | C$_7$H$_5$ClF | 2 |
| 131 | C$_6$H$_3$ClF | 3 |
| 129 | C$_6$H$_3$ClF | 9 |

Example 8

The Preparation of 1,2,3,7,8,9-hexachlorofluorodibenzofuran 1 mmol, corresponding to 0.375 g, of 1,2,3,7,8,9-hexachlorodibenzofuran were dissolved in 50 ml of acetic anhydride with heating. Thereafter, the nitric acid nitrating reagent (0.11 g; 63% by weight; 10 percent excess) in 10 ml of acetic anhydride were added. After the reaction had abated, the reaction mixture was poured onto 100 g of ice with vigorous stirring. The resulting crude product, 1,2,3,7,8,9-hexachloro-4-nitrodibenzofuran, was filtered off with suction and recrystallized from acetic acid.

The corresponding amine was prepared by reducing 1,2,3,7,8,9-hexachloro-4-nitrodibenzofuran with 1.8 mmol of NaSH in 5 ml of ethanol. The resulting 1,2,3,7,8,9-hexachloro-4-aminodibenzofuran was isolated by extracting with five times 30 ml of diethyl ether. The resulting solution was washed twice with 10 ml of water and dried over magnesium sulfate. Subsequently, the amine was removed from the desiccant and isolated again.

1,2,3,7,8,9-Hexachloro-4-aminodibenzofuran was converted to the corresponding diazonium compound by the reaction with 1.1 mmol of nitrite (dissolved in 2 ml of water). The counteranion was exchanged for the tetrafluoroborate anion by repeatedly slurrying the diazonium compound at −20° C. in four times 20 ml in each case of 20% by weight HBF$_4$. The resulting Schiemann was decomposed to result in the corresponding fluorine compound, 1,2,3,7,8,9-hexachloro-4-fluorodibenzofuran. After the purification, 0.263 g of the product, corresponding to 67% yield, was obtained, and was characterized by mass spectrometry (cf. Table 3).

1,2,3,7,8,9-Hexachloro-4-fluorodibenzofuran was usable in an outstanding manner in the analysis of halogenated dibenzofurans.

TABLE 3

Mass spectrum of 1,2,3,7,8,9-hexachloro-4-fluorodibenzofuran

| m/z | Ion | Intensity (%) |
|---|---|---|
| 398 | M$^+$ | 8 |
| 396 | M$^+$ | 34 |
| 394 | M$^+$ | 80 |
| 392 | M$^+$ | 100 |
| 390 | M$^+$ | 52 |
| 361 | M$^+$—Cl | 2 |
| 359 | M$^+$—Cl | 5 |
| 357 | M$^+$—Cl | 7 |
| 355 | M$^+$—Cl | 4 |
| 326 | M$^+$—Cl$_2$ | 4 |
| 324 | M$^+$—Cl$_2$ | 17 |
| 322 | M$^+$—Cl$_2$ | 35 |
| 320 | M$^+$—Cl$_2$ | 28 |
| 289 | M$^+$—Cl$_2$—Cl | 1 |
| 287 | M$^+$—Cl$_2$—Cl | 3 |
| 285 | M$^+$—Cl$_2$—Cl | 3 |
| 254 | M$^+$—Cl$_2$—Cl$_2$ | 3 |
| 252 | M$^+$—Cl$_2$—Cl$_2$ | 17 |
| 250 | M$^+$—Cl$_2$—Cl$_2$ | 26 |
| 217 | M$^+$—Cl$_2$—Cl$_2$—Cl | 1 |
| 215 | M$^+$—Cl$_2$—Cl$_2$—Cl | 3 |
| 180 | M$^+$—Cl$_2$—Cl$_2$—Cl$_2$ | 15 |
| 160 | M$^+$—Cl$_2$—Cl$_2$—Cl$_2$—HF | 1 |
| 198 | M$^{++}$ | 2 |
| 197 | M$^{++}$ | 5 |
| 196 | M$^{++}$ | 8 |
| 195 | M$^{++}$ | 3 |

Examples 9 and 10

The Preparation of 2,3,7,8-tetrachloro-1-fluorodibenzo-p-dioxin (Example 9) and 1,4,6,9-tetrachloro-2-fluorodibenzo-p-dioxin (Example 10)

For Example 9, Example 8 was repeated, except that 2,3,7,8-tetrachlorodibenzo-p-dioxin was used as the starting material in place of 1,2,3,7,8,9-hexachlorodibenzofuran. 0.211 g of 2,3,7,8-tetrachloro-1-fluorodibenzo-p-dioxin was obtained, corresponding to a yield of 62%, and was characterized by mass spectrometry (cf. Table 4).

For Example 10, Example 8 was repeated, except that 1,4,6,9-tetrachlorodibenzo-p-dioxin was used as the starting material in place of 1,2,3,7,8,9-hexachlorodibenzofuran. 0.221 g of 1,4,6,9-tetrachloro-2-fluorodibenzo-p-dioxin, corresponding to a yield of 65%, was obtained, and was characterized by mass spectrometry (cf. Table 5).

Both compounds were usable in an outstanding manner in the analysis of chlorinated dibenzo-p-dioxins.

TABLE 4

Mass spectrum of 2,3,7,8-tetrachloro-1-fluorodibenzo-p-dioxin

| m/z | Ion | Intensity (%) |
|---|---|---|
| 344 | M$^+$ | 10 |
| 342 | M$^+$ | 48 |
| 340 | M$^+$ | 100 |
| 338 | M$^+$ | 78 |
| 307 | M$^+$—Cl | 2 |
| 305 | M$^+$—Cl | 6 |
| 303 | M$^+$—Cl | 7 |
| 272 | M$^+$—Cl$_2$ | 4 |
| 270 | M$^+$—Cl$_2$ | 23 |
| 286 | M$^+$—Cl$_2$ | 36 |
| 235 | M$^+$—Cl$_2$—Cl | 1 |
| 233 | M$^+$—Cl$_2$—Cl | 4 |
| 198 | M$^+$—Cl$_2$—Cl$_2$ | 28 |
| 178 | M$^+$—Cl$_2$—Cl$_2$—HF | 3 |
| 170 | M$^{++}$ | 11 |
| 169 | M$^{++}$ | 9 |

TABLE 5

Mass spectrum of 1,4,6,9-tetrachloro-2-fluorodibenzo-p-dioxin

| m/z | Ion | Intensity (%) |
|---|---|---|
| 344 | M$^+$ | 9 |
| 342 | M$^+$ | 46 |
| 340 | M$^+$ | 100 |
| 338 | M$^+$ | 77 |
| 307 | M$^+$—Cl | 1 |
| 305 | M$^+$—Cl | 7 |
| 303 | M$^+$—Cl | 8 |
| 272 | M$^+$—Cl$_2$ | 3 |
| 270 | M$^+$—Cl$_2$ | 22 |
| 286 | M$^+$—Cl$_2$ | 35 |
| 235 | M$^+$—Cl$_2$—Cl | 1 |
| 233 | M$^+$—Cl$_2$—Cl | 4 |
| 198 | M$^+$—Cl$_2$—Cl$_2$ | 29 |
| 178 | M$^+$—Cl$_2$—Cl$_2$—HF | 2 |
| 170 | M$^{++}$ | 10 |
| 169 | M$^{++}$ | 8 |

Example 11

The Preparation of 2',3,3',4,5,5',6,6'-octabromo-2,4'-difluorodiphenyl ether

The compound was synthesized by the Lewis acid-catalyzed bromination of 2,4'-difluorodiphenyl ether. 2,4'-Difluorodiphenyl ether was obtained by the Ullmann reaction of 4-fluorophenol with 2-bromofluorobenzene.

2,4'-Difluorodiphenyl ether

4-Fluorophenol (1.12 g, 10 mmol) was heated to 50° C. KOH (0.56 g, 10 mmol) was added thereto, and the reaction mixture was stirred over 10 min. 2-Bromofluorobenzene (1.75 g, 10 mmol) and powdered copper (0.64 g) were added thereto. The reaction mixture was stirred at 110° C. over a further 2 hours. Unconverted 2-bromofluorobenzene was removed by means of vacuum distillation. The product was subsequently purified on a silica gel-packed column with n-hexane as the mobile phase. Yield: 1.0 g (4.8 mmol, 48%) of the product with a purity of 97.3%, determined by means GC. $^1$H NMR: δ 6.92-7.21 multiple peaks. $^{13}$C NMR: δ 158.0 (d, $^1J_{C-F}$=341.2, C-4'), 154.8 (d, $^1J_{C-F}$=348.5, C-2), 153.2 (d, $^4J_{C-F}$=3.1, C-1'), 144.2 (d, $^2J_{C-F}$=11.3, C-1), 124.7 (m, C-6, C-2' and C-6'), 121.3 (d, $^4J_{C-F}$=1.7, C-5), 118.9 (d, $^3J_{C-F}$=8.3, C-4), 117.1 (d, $^2J_{C-F}$=18.3, C-3), 116.2 (d, $^2J_{C-F}$=23.8, C-3' and C-5').

2',3,3',4,5,5',6,6'-Octabromo-2,4'-difluorodiphenyl ether

Bromine (1.4 ml, 27.2 mmol) was dissolved in 1,2-dichloroethane (6 ml) and added dropwise slowly to a mixture of 2,4'-difluorodiphenyl ether (0.5 g; 2.43 mmol) and AlCl$_3$ (0.04 g; 0.3 mmol) dissolved in 1,2-dichloroethane (5 ml). The reaction mixture was then stirred at 75° C. overnight. Subsequently, the reaction was ended by adding an aqueous NaHSO$_3$ solution (2 g/10 ml). The organic phase was removed, washed with water and dried over Na$_2$SO$_4$. The solvent was subsequently removed on a rotary evaporator. The resulting product was purified by recrystallization from CH$_2$Cl$_2$. Yield: 0.6 g (0.72 mmol), 29%). $^{13}$C NMR: δ 154.0 (d, $^1J_{C-F}$=325.5, C-4'), 150.0 (d, $^1J_{C-F}$=330.9, C-2), 148.1 (s, C-1'), 140.2 (d, $^2J_{C-F}$=15.5, C-1), 125.1 (d, $^3J_{C-F}$=5.9, C-6, C-2' and C-6'), 122.9 (s, C-5), 119.0 (d, $^3J_{C-F}$=5.9, C-4), 118.1 (d, $^2J_{C-F}$=7.8, C-3), 113.3 (d, $^2J_{C-F}$=34.2, C-3' and C-5').

Example 12

The Preparation of 2',4',4-trichloro-3,5-difluorobiphenyl

Under an inert gas blanket, 5 ml of an aqueous, two molar sodium carbonate solution were added to a solution of 5 mmol of 1,3-difluoro-2-chloro-5-bromobenzene and 0.18 mg of Pd(PPh$_3$)$_4$ in 20 ml of toluene. A solution of 5 mmol of 2,4-dichlorobenzeneboric acid in 10 ml of ethanol was added to the resulting mixture under an inert gas blanket. The reaction mixture was heated to 80° C. under inert gas over one hour. Thereafter, the reaction was ended by adding 0.5 ml of Perhydrol. Subsequently, the reaction mixture was stirred over another 4 hours, after which it was taken up with 20 ml of diethyl ether. The water-soluble constituents of the resulting mixture were removed by shaking with water. The removed organic phase was dried with magnesium sulfate. After the desiccant had been removed, the organic solution was concentrated by evaporation and the resulting crude product was purified by recrystallization. The recrystallized product was characterized by mass spectrometry (cf. Table 6).

2',4'-Trichloro-3,5-difluorobiphenyl was usable in an outstanding manner in the analysis of chlorinated biphenyls.

TABLE 6

Mass spectrum of 2',4',4-trichloro-3,5-difluorobiphenyl

| m/z | Ion | Intensity (%) |
|---|---|---|
| 298 | M$^+$(C$_{12}$H$_5$Cl$_3$F$_2$) | 3 |
| 296 | M$^+$ | 31 |
| 294 | M$^+$ | 96 |
| 292 | M$^+$ | 100 |
| 261 | M$^+$—Cl | 1 |
| 259 | M$^+$—Cl | 4 |
| 257 | M$^+$—Cl | 7 |
| 224 | M$^+$—Cl$_2$ | 14 |
| 222 | M$^+$—Cl$_2$ | 43 |
| 187 | M$^+$—Cl$_2$—Cl | 32 |
| 146 | M$^{++}$ | 7 |

Example 13

The Preparation of 4-methyl-2,2',5,6-tetrachloro-3',5'-difluorodiphenylmethane and 4-methyl-2,2',5,6-tetrachloro-3,3'-difluorodiphenylmethane 4-Methyl-2,2',5,6-tetrachlorodiphenylmethane was fluorinated directly with Fluorselect® in an inert organic solvent. Subsequently, any Fluorselect® still present was reduced. The water-soluble constituents of the resulting mixture were removed by shaking with water. The organic phase was dried with magnesium sulfate. After the desiccant had been removed, the organic phase was concentrated by evaporation. 4-Methyl-2,2',5,6-tetrachloro-3'-fluorodiphenylmethane was fluorinated directly once more with Fluorselect® in an inert organic solvent. The reaction mixture is then stirred at room temperature for 120 hours. Subsequently, any Fluorselect® still present was reduced. The water-soluble constituents of the resulting mixture were removed by shaking with water. The organic phase was dried with magnesium sulfate. After the desiccant had been removed, the organic phase was concentrated by evaporation and the resulting crude product was purified by recrystallization. This affords two isomers, 4-methyl-2,2',5,6-tetrachloro-3',5'-difluorodiphenylmethane and 4-methyl-2,2',5,6-tetrachloro-3,3'-difluorodiphenylmethane, which can be separated from one another by repeated zone melting. The products are then characterized by mass spectrometry (cf. Tables 7 and 8). 4-Methyl-2,2',5,6-tetrachloro-3',5'-difluorodiphenylmethane and 4-methyl-2,2',5,6-tetrachloro-3,3'-difluorodiphenylmethane were usable in an outstanding manner in the analysis of chlorinated diphenylmethanes (UGILEC®).

TABLE 7

Mass spectrum of 4-methyl-2,2',5,6-tetrachloro-3',5'-difluorodiphenylmethane

| m/z | Ion | Intensity (%) |
|---|---|---|
| 360 | M$^+$(C$_{14}$H$_8$Cl$_4$F$_2$) | 9 |
| 358 | M$^+$ | 47 |
| 356 | M$^+$ | 100 |
| 354 | M$^+$ | 78 |
| 339 | M$^+$—CH$_3$ | 2 |
| 323 | M$^+$—Cl | 2 |
| 321 | M$^+$—Cl | 5 |
| 319 | M$^+$—Cl | 7 |
| 304 | M$^+$—Cl—CH$_3$ | 2 |
| 288 | M$^+$—Cl$_2$ | 4 |
| 286 | M$^+$—Cl$_2$ | 23 |
| 284 | M$^+$—Cl$_2$ | 34 |
| 269 | M$^+$—Cl$_2$—CH$_3$ | 4 |
| 251 | M$^+$—Cl$_2$—Cl | 1 |
| 249 | M$^+$—Cl$_2$—Cl | 4 |
| 234 | M$^+$—Cl$_2$—Cl—CH$_3$ | 2 |
| 214 | M$^+$—Cl$_2$—Cl$_2$ | 27 |
| 209 | C$_8$H$_6$Cl$_3$ | 9 |
| 207 | C$_8$H$_6$Cl$_3$ | 7 |
| 194 | M$^+$—Cl$_2$—Cl$_2$—HF | 2 |
| 192 | C$_7$H$_4$Cl$_3$ | 8 |
| 190 | C$_7$H$_4$Cl$_3$ | 7 |
| 191 | M$^+$—Cl$_2$—Cl$_2$—CH$_3$ | 2 |
| 178 | M$^{++}$ | 11 |
| 177 | M$^{++}$ | 9 |
| 163 | C$_7$H$_4$ClF$_2$ | 2 |
| 161 | C$_7$H$_4$ClF$_2$ | 6 |
| 149 | C$_6$H$_2$ClF$_2$ | 4 |
| 147 | C$_6$H$_2$ClF$_2$ | 9 |

TABLE 8

Mass spectrum of 4-methyl-2,2',5,6-tetrachloro-3,3'-difluorodiphenylmethane

| m/z | Ion | Intensity (%) |
|---|---|---|
| 360 | $M^+(C_{14}H_8Cl_4F_2)$ | 7 |
| 358 | $M^+$ | 47 |
| 356 | $M^+$ | 100 |
| 354 | $M^+$ | 78 |
| 339 | $M^+—CH_3$ | 3 |
| 323 | $M^+—Cl$ | 2 |
| 321 | $M^+—Cl$ | 5 |
| 319 | $M^+—Cl$ | 7 |
| 304 | $M^+—Cl—CH_3$ | 2 |
| 288 | $M^+—Cl_2$ | 4 |
| 286 | $M^+—Cl_2$ | 23 |
| 284 | $M^+—Cl_2$ | 35 |
| 269 | $M^+—Cl_2—CH_3$ | 4 |
| 251 | $M^+—Cl_2—Cl$ | 1 |
| 249 | $M^+—Cl_2—Cl$ | 4 |
| 234 | $M^+—Cl_2—Cl—CH_3$ | 2 |
| 227 | $C_8H_5Cl_3F$ | 9 |
| 225 | $C_8H_5Cl_3F$ | 7 |
| 214 | $M^+—Cl_2—Cl_2$ | 27 |
| 213 | $C_7H_3Cl_3F$ | 7 |
| 211 | $C_7H_3Cl_3F$ | 5 |
| 194 | $M^+—Cl_2—Cl_2—HF$ | 2 |
| 191 | $M^+—Cl_2—Cl_2—CH_3$ | 2 |
| 178 | $M^{++}$ | 11 |
| 177 | $M^{++}$ | 9 |
| 145 | $C_7H_5ClF$ | 2 |
| 143 | $C_7H_5ClF$ | 6 |
| 131 | $C_6H_3ClF$ | 5 |
| 129 | $C_6H_3ClF$ | 9 |

Example 14

The Preparation of 1,2,3,7,8,9-hexachloro-4,6-difluorodibenzofuran 1 mmol, corresponding to 0.375 g, of 1,2,3,7,8,9-hexachlorodibenzofuran were dissolved in 50 ml of acetic anhydride with heating. Thereafter, the nitric acid nitrating reagent (0.25 g; 63% by weight; 25 percent excess) in 10 ml of acetic anhydride were added. After the reaction had abated, the reaction mixture was poured onto 100 g of ice with vigorous stirring. The resulting crude product, 1,2,3,7,8,9-hexachloro-4,6-dinitrodibenzofuran, was filtered off with suction and recrystallized from acetic acid.

The corresponding amine was prepared by reducing 1,2,3,7,8,9-hexachloro-4,6-dinitrodibenzofuran with 3.6 mmol of NaSH in 5 ml of ethanol. The resulting 1,2,3,7,8,9-hexachloro-4,6-diaminodibenzofuran was isolated by extracting with five times 30 ml of diethyl ether. The resulting solution was washed twice with 10 ml of water and dried over magnesium sulfate. Subsequently, the amine was removed from the desiccant and isolated again.

1,2,3,7,8,9-Hexachloro-4,6-diaminodibenzofuran was converted to the corresponding diazonium compound by the reaction with 2.2 mmol of nitrite (dissolved in 3 ml of water). The counteranion was exchanged for the tetrafluoroborate anion by repeatedly slurrying the diazonium compound at −20° C. in four times 20 ml in each case of 20% by weight $HBF_4$. The resulting Schiemann salt was decomposed to result in the corresponding fluorine compound, 1,2,3,7,8,9-hexachloro-4,6-difluoro-dibenzofuran. After the purification, 0.221 g of the product, corresponding to 56% yield, was obtained, and was characterized by mass spectrometry (cf. Table 8).

1,2,3,7,8,9-Hexachloro-4,6-difluorodibenzofuran was usable in an outstanding manner in the analysis of halogenated dibenzofurans.

TABLE 8

Mass spectrum of 1,2,3,7,8,9-hexachloro-4,6-fluoro-dibenzofuran

| m/z | Ion | Intensity (%) |
|---|---|---|
| 416 | $M^+(C_{12}Cl_6F_2O)$ | 8 |
| 414 | $M^+$ | 33 |
| 412 | $M^+$ | 79 |
| 410 | $M^+$ | 100 |
| 408 | $M^+$ | 53 |
| 379 | $M^+—Cl$ | 2 |
| 377 | $M^+—Cl$ | 5 |
| 375 | $M^+—Cl$ | 8 |
| 373 | $M^+—Cl$ | 4 |
| 344 | $M^+—Cl_2$ | 4 |
| 342 | $M^+—Cl_2$ | 19 |
| 340 | $M^+—Cl_2$ | 33 |
| 338 | $M^+—Cl_2$ | 28 |
| 307 | $M^+—Cl_2—Cl$ | 1 |
| 305 | $M^+—Cl_2—Cl$ | 3 |
| 303 | $M^+—Cl_2—Cl$ | 3 |
| 272 | $M^+—Cl_2—Cl_2$ | 3 |
| 270 | $M^+—Cl_2—Cl_2$ | 18 |
| 268 | $M^+—Cl_2—Cl_2$ | 24 |
| 235 | $M^+—Cl_2—Cl_2—Cl$ | 1 |
| 233 | $M^+—Cl_2—Cl_2—Cl$ | 3 |
| 210 | $M^{++}$ | 2 |
| 208 | $M^{++}$ | 6 |
| 206 | $M^{++}$ | 8 |
| 204 | $M^{++}$ | 3 |
| 198 | $M^+—Cl_2—Cl_2—Cl_2$ | 15 |
| 160 | $M^+—Cl_2—Cl_2—Cl_2—F_2$ | 1 |

Example 15

The Preparation of 1,2,3,7,8,9-hexachloro-4,6-difluorodibenzo-p-dioxin

For Example 15, Example 14 was repeated, except that 1,2,3,7,8,9-hexachlorodibenzo-p-dioxin was used as the starting material in place of 1,2,3,7,8,9-hexachlorodibenzofuran. 0.203 g of 1,2,3,7,8,9-hexachloro-4,6-difluorodibenzo-p-dioxin, corresponding to a yield of 47%, was obtained, and was characterized by mass spectrometry (cf. Table 9).

1,2,3,7,8,9-Hexachloro-4,6-difluorodibenzo-p-dioxin is usable in an outstanding manner in the analysis of chlorinated dibenzo-p-dioxins.

TABLE 9

Mass spectrum of 1,2,3,7,8,9-hexachloro-4,6-difluoro-dibenzo-p-dioxin

| m/z | Ion | Intensity (%) |
|---|---|---|
| 432 | $M^+(C_{12}Cl_6F_2O_2)$ | 8 |
| 430 | $M^+$ | 35 |
| 428 | $M^+$ | 79 |
| 426 | $M^+$ | 100 |
| 424 | $M^+$ | 53 |
| 393 | $M^+—Cl$ | 2 |
| 392 | $M^+—Cl$ | 6 |
| 391 | $M^+—Cl$ | 8 |
| 389 | $M^+—Cl$ | 4 |
| 360 | $M^+—Cl_2$ | 4 |
| 358 | $M^+—Cl_2$ | 21 |

TABLE 9-continued

Mass spectrum of 1,2,3,7,8,9-hexachloro-4,6-difluoro-dibenzo-p-dioxin

| m/z | Ion | Intensity (%) |
|---|---|---|
| 356 | $M^+$—$Cl_2$ | 33 |
| 354 | $M^+$—$Cl_2$ | 28 |
| 319 | $M^+$—$Cl_2$—$Cl$ | 1 |
| 317 | $M^+$—$Cl_2$—$Cl$ | 3 |
| 315 | $M^+$—$Cl_2$—$Cl$ | 4 |
| 288 | $M^+$—$Cl_2$—$Cl_2$ | 3 |
| 286 | $M^+$—$Cl_2$—$Cl_2$ | 18 |
| 284 | $M^+$—$Cl_2$—$Cl_2$ | 24 |
| 251 | $M^+$—$Cl_2$—$Cl_2$—$Cl$ | 1 |
| 249 | $M^+$—$Cl_2$—$Cl_2$—$Cl$ | 2 |
| 214 | $M^+$—$Cl_2$—$Cl_2$—$Cl_2$ | 14 |
| 215 | $M^{++}$ | 2 |
| 214 | $M^{++}$ | 6 |
| 213 | $M^{++}$ | 7 |
| 212 | $M^{++}$ | 3 |
| 176 | $M^+$—$Cl_2$—$Cl_2$—$Cl_2$—$F_2$ | 1 |

We claim:

1. A method of analyzing halogenated organic compounds, comprising the steps of: providing the following compounds
4'-fluoro-2,3',4-tribromodiphenylether,
4'-fluoro-2,3',6-tribromodiphenylether,
4'-fluoro-2,3',4,6-tetrabromodiphenylether,
4'-fluoro-2,3,3',4,5,6-hexabromodiphenylether,
2'3,3',4,5,5',6,6'-octabromo-2,4'-difluoro-diphenylether,
2,4,4'-trichloro-3'-fluorobiphenyl,
2',4',4-trichloro-3,5-difluorobiphenyl,
4-methyl-2,2',5,6-tetrachloro-3'-fluoro-diphenylmethane,
4-methyl-2,2',5,6-tetrachloro-3',5'-difluoro-diphenylmethane,
4-methyl-2,2',5,6-tetrachloro-3',3'-difluoro-diphenylmethane,
1,2,3,7,8,9-hexachloro-4-fluoro-dibenzofuran
1,2,3,7,8,9-hexachloro-4,6-difluoro-dibenzofuran
2,3,7,8-tetrachloro-1-fluoro-dibenzo-p-dioxin
1,4,6,9-tetrachloro-2-fluoro-dibenzo-p-dioxin and
1,2,3,7,8,9-hexachloro-4,6-difluoro-dibenzo-p-dioxin;
selecting at least one of the compounds; and
analyzing a halogenated organic compound by using at least one of the selected compounds
as intern standards or surrogate standards which together with their base compounds undergo physical, chemical and/or biological processes and are subsequently detected and/or analyzed together with the processes or separately from the processes,
as external standards, which instead of their base compounds undergo physical, chemical and/or biological processes for the purpose of calibrating these processes and are analyzed and/or detected separately from the base compounds,
and/or undergo instead of their base compounds chemical and/or biological processes as model compounds for the purpose of detecting reaction mechanisms whose reaction products are detected and/or analyzed.

2. A method of analyzing according to claim 1, including using the analytical compound in halogen organic compounds.

3. The method according to claim 1, wherein the base compounds are the congeneric, chlorinated and brominated diphenylethers, biphenyls, diphenylmethanes, dibenzofuranes, and dibenzo-p-dioxins.

* * * * *